(12) United States Patent
Martin

(10) Patent No.: US 10,278,837 B1
(45) Date of Patent: May 7, 2019

(54) COMPLIANT FORCE DISTRIBUTION SYSTEM

(71) Applicant: James Jay Martin, Oklahoma City, OK (US)

(72) Inventor: James Jay Martin, Oklahoma City, OK (US)

( * ) Notice: Subject to any disclaimer, the term of this patent is extended or adjusted under 35 U.S.C. 154(b) by 0 days.

(21) Appl. No.: 14/804,985

(22) Filed: Jul. 21, 2015

Related U.S. Application Data

(63) Continuation-in-part of application No. 14/164,426, filed on Jan. 27, 2014, now abandoned.

(60) Provisional application No. 61/849,509, filed on Jan. 28, 2013.

(51) Int. Cl.
*A61F 5/00* (2006.01)
*A61F 2/80* (2006.01)
*A61F 2/78* (2006.01)
*A61F 2/54* (2006.01)

(52) U.S. Cl.
CPC ............... *A61F 2/80* (2013.01); *A61F 2/54* (2013.01); *A61F 2/78* (2013.01); *A61F 2002/7862* (2013.01)

(58) Field of Classification Search
CPC .......... A61F 5/0102; A61F 5/028; A61F 5/01; A61F 5/0123; A61F 5/0118; A61F 5/0125; A61F 5/0109; A61F 5/02; A61F 2002/745; A61F 2002/747; A61F 2005/0167; A61F 2/68; A61F 5/024; A61F 5/3738; A61H 1/024; A61H 2201/1246; A61H 2201/149; A61H 2201/165; A61H 2201/5061; A61H 2201/5084; A61H 3/00; A61H 2201/501; A61H 1/0244; A61H 1/0266; A61H 2201/1215; A61H 2201/1238; A61H 2201/1261; A61B 17/7031; A61B 17/7058; A61B 2090/064; A61B 2560/0223; A61B 2560/0276; A61B 2560/0475; A61B 2562/0247; A61B 2562/08; A61B 5/0031; A61B 5/103; A61B 5/1038; A61B 5/4836; A61B 5/4851
See application file for complete search history.

(56) References Cited

U.S. PATENT DOCUMENTS

| | | | |
|---|---|---|---|
| 1,638,704 A * | 8/1927 | Pope | A61F 5/04 450/147 |
| 2,008,201 A | 7/1935 | Chute | |
| 2,994,322 A * | 8/1961 | Cullen | A61F 5/0111 450/41 |
| 3,827,612 A | 8/1974 | Mead et al. | |
| 4,960,135 A * | 10/1990 | Nelson | A61F 5/0111 602/27 |
| 7,021,508 B1 | 4/2006 | Aston | |
| 7,611,477 B2 * | 11/2009 | Dayhoff | A61F 5/0113 602/27 |
| 8,240,532 B2 | 8/2012 | Cragg | |
| 8,840,681 B2 | 9/2014 | Martin et al. | |
| 8,858,482 B2 * | 10/2014 | Ingimundarson | A61F 5/0111 128/882 |

(Continued)

*Primary Examiner* — Kim M Lewis
(74) *Attorney, Agent, or Firm* — Phillips Murrah PC; Martin G. Ozinga

(57) ABSTRACT

The invention is an apparatus, system, and or method that provides a compliant force distribution interface system for prosthetics or orthotics users, to suspend force loads around such user's body segments by utilizing a compliant fabric member adapted for positioning around the user's body segments.

3 Claims, 28 Drawing Sheets

(56) References Cited

U.S. PATENT DOCUMENTS

| | | | |
|---|---|---|---|
| 2006/0004311 A1* | 1/2006 | Hargrave | A61F 5/0111 |
| | | | 602/5 |
| 2007/0027419 A1* | 2/2007 | Drennan | A61F 5/0193 |
| | | | 602/19 |
| 2008/0010730 A1 | 1/2008 | Twito et al. | |
| 2009/0084821 A1 | 4/2009 | Lenzi | |
| 2009/0282595 A1 | 11/2009 | Branson et al. | |
| 2010/0256544 A1* | 10/2010 | Colon | A61F 5/05 |
| | | | 602/28 |
| 2011/0082403 A1* | 4/2011 | Hill | A61F 5/0113 |
| | | | 602/28 |
| 2011/0180579 A1 | 7/2011 | Richardson | |
| 2015/0045709 A1* | 2/2015 | Wiley | A61F 5/0111 |
| | | | 602/28 |

\* cited by examiner

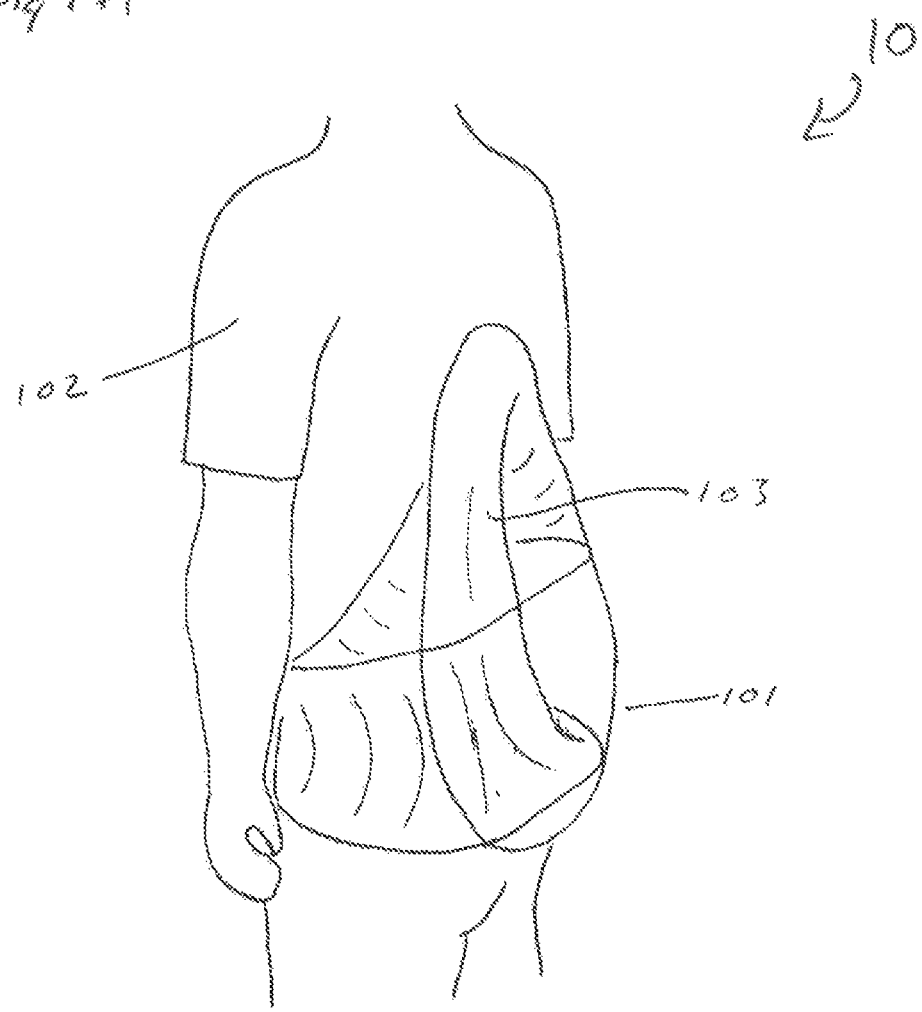

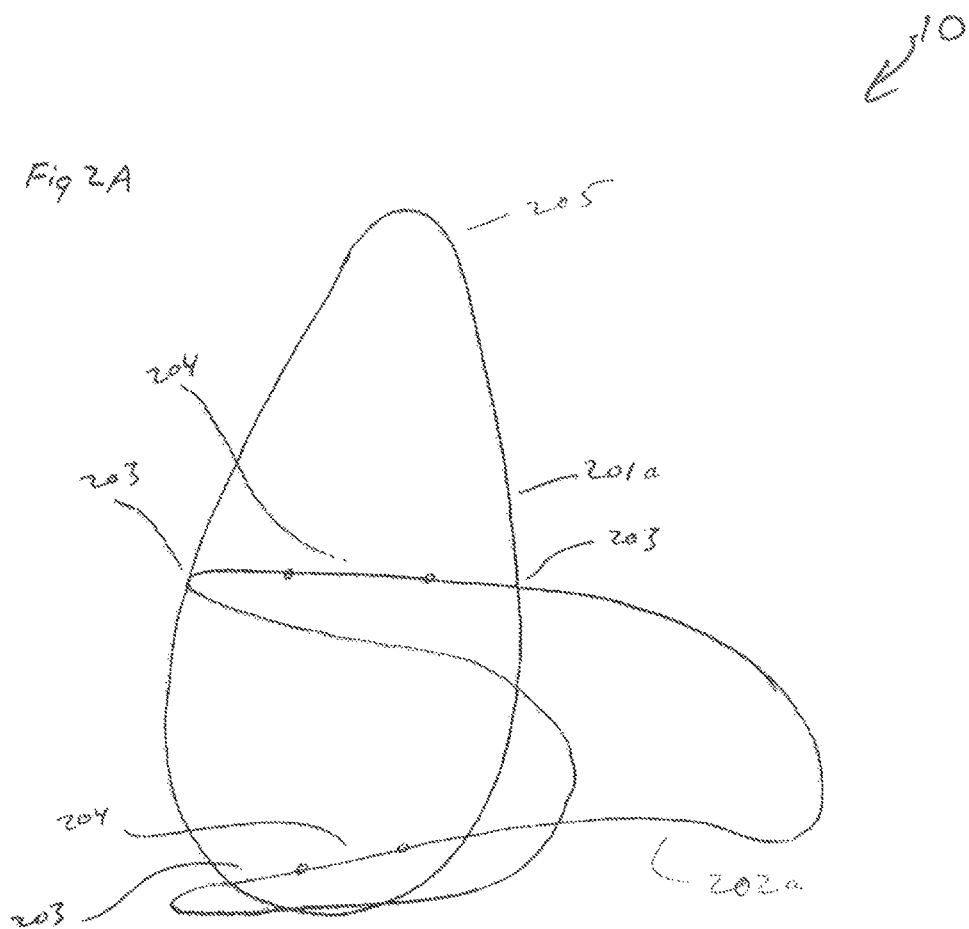

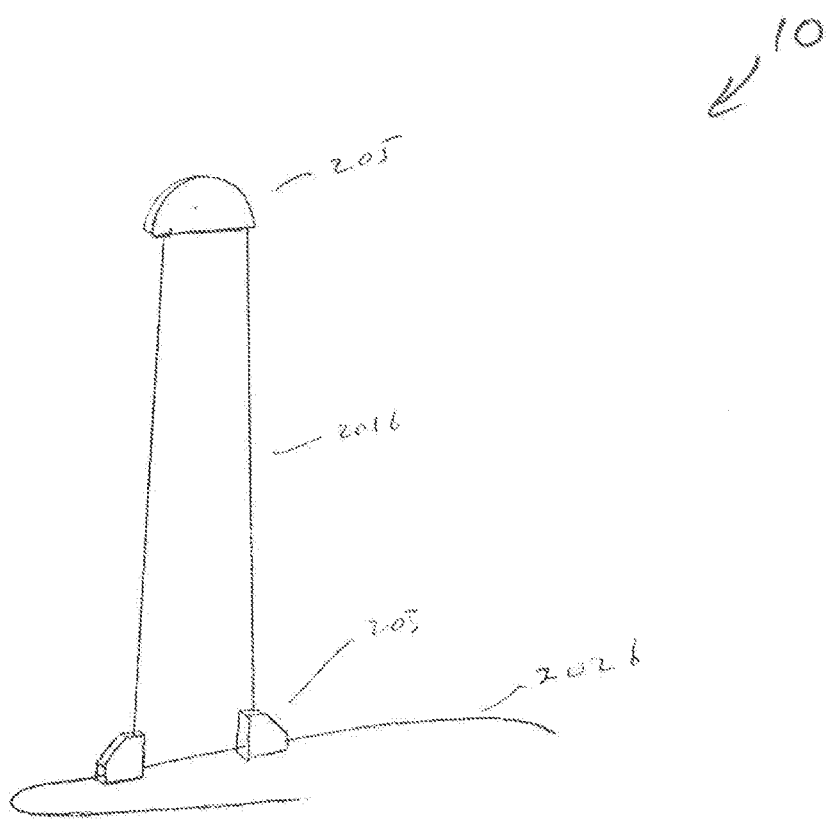

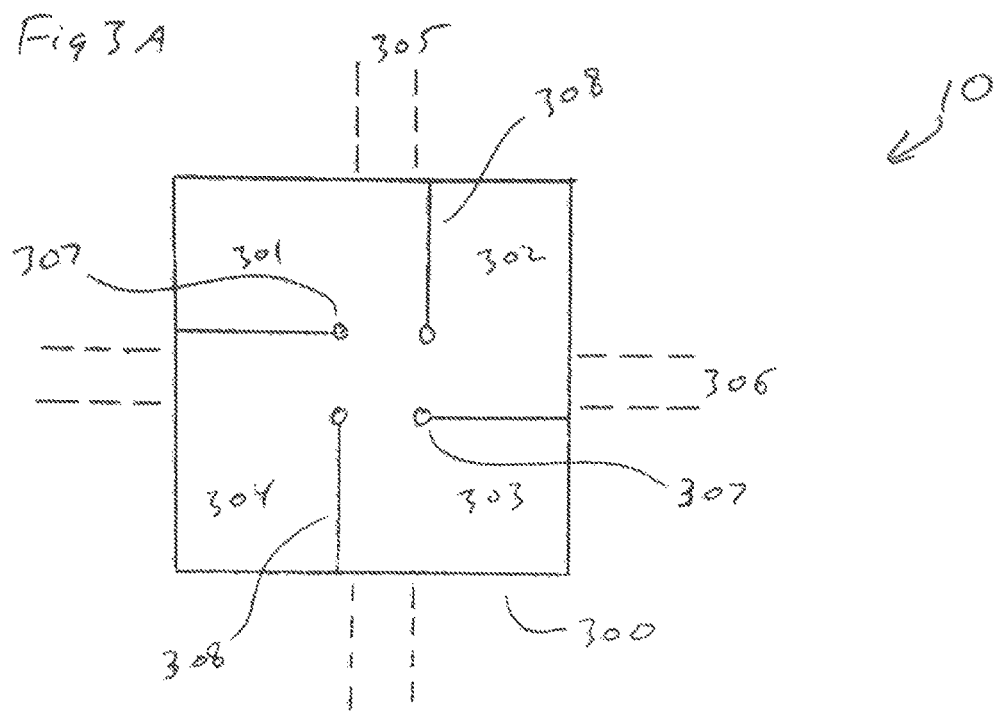

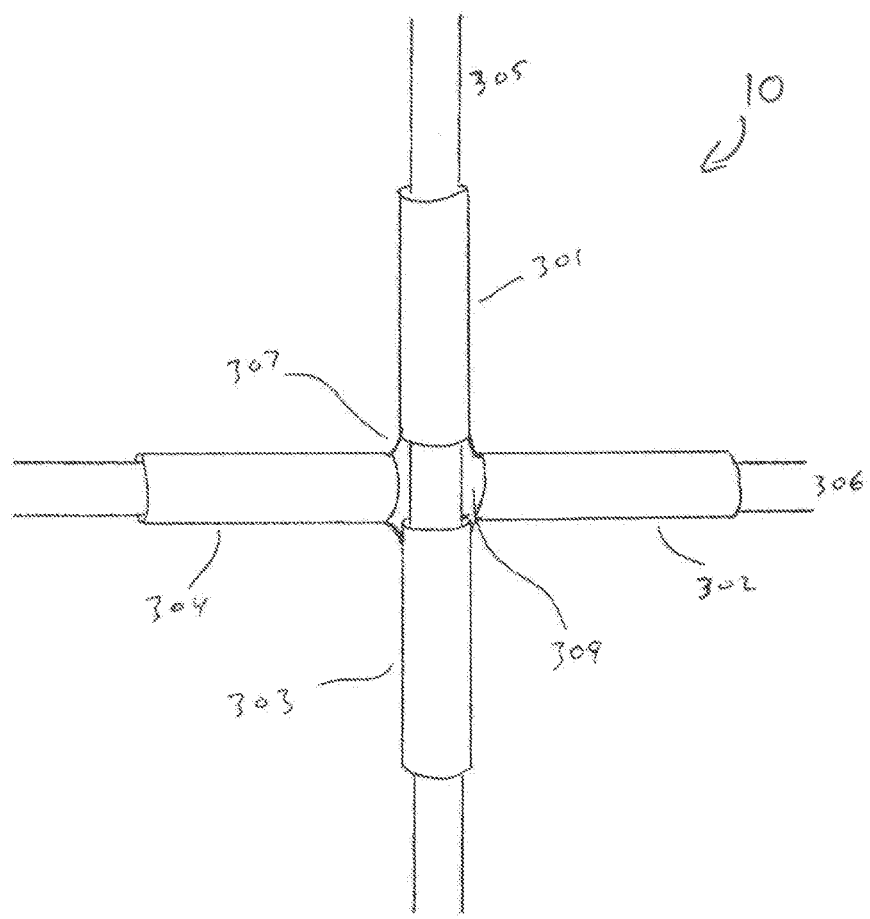

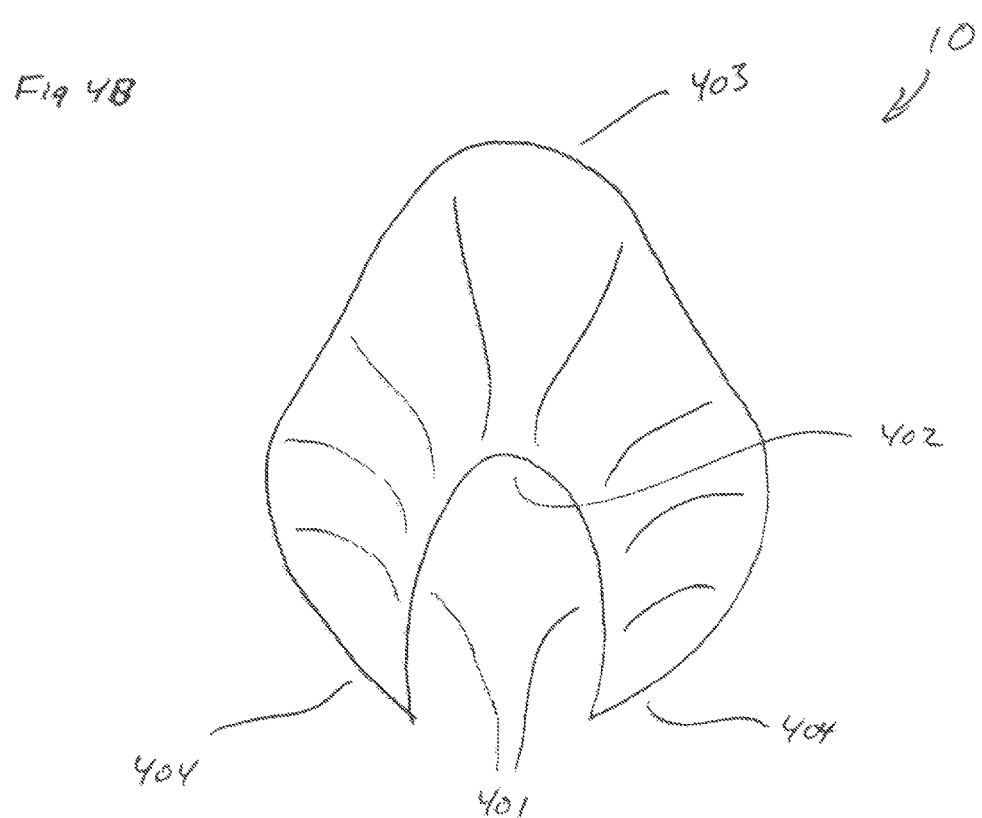

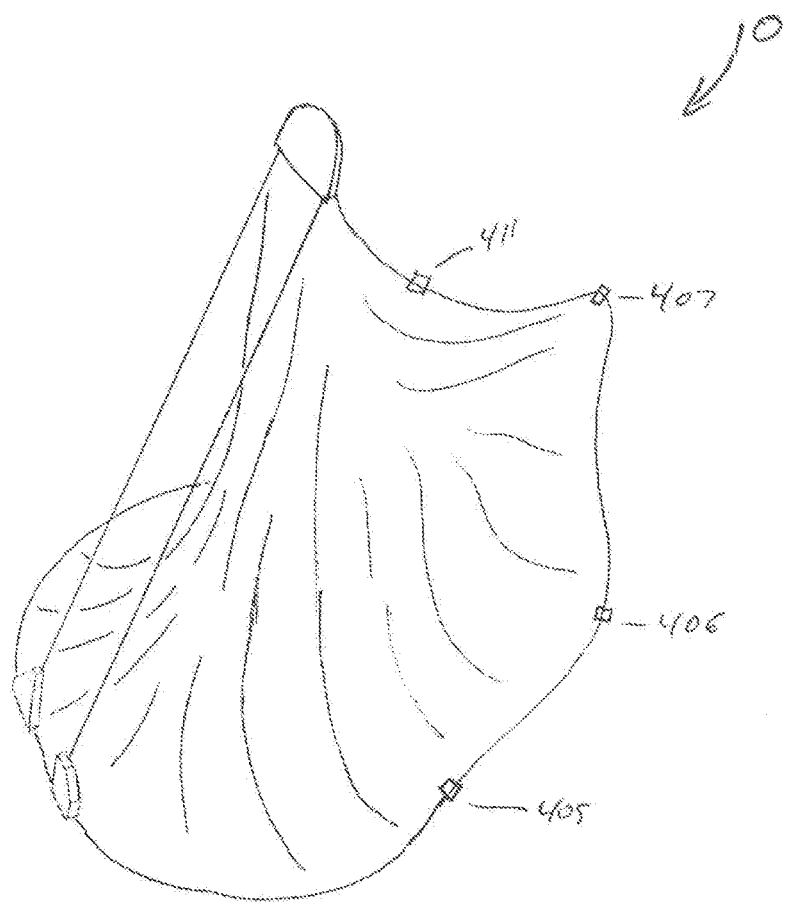

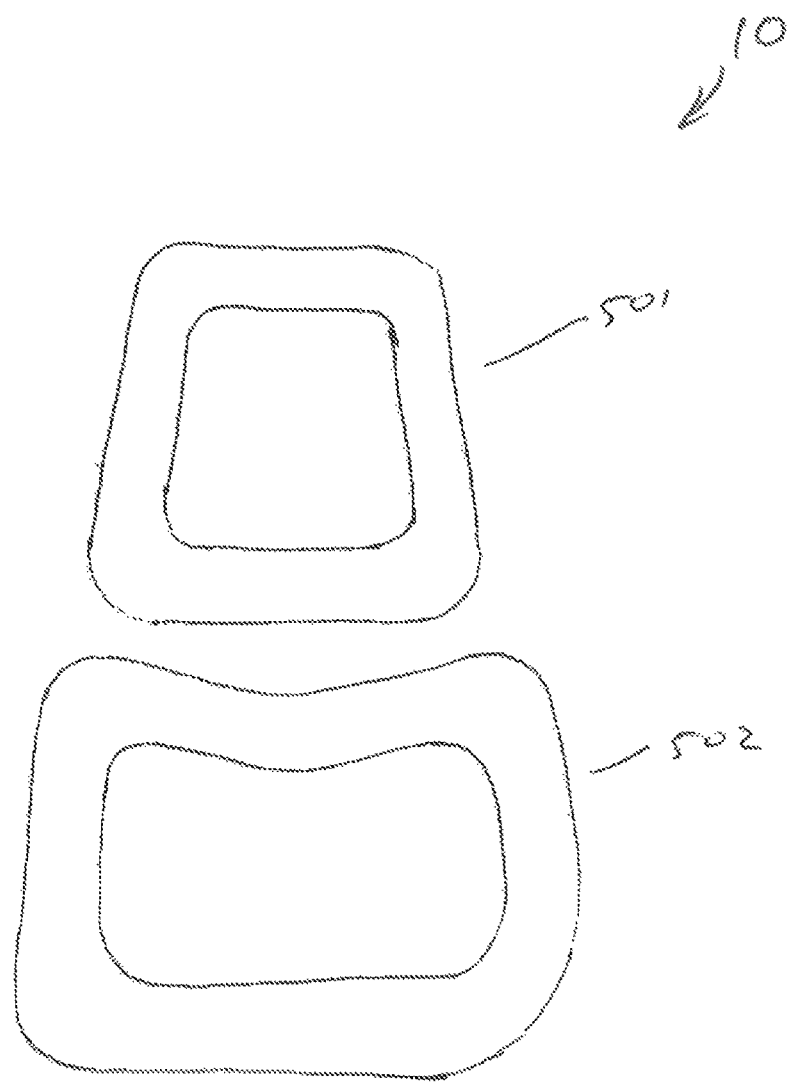

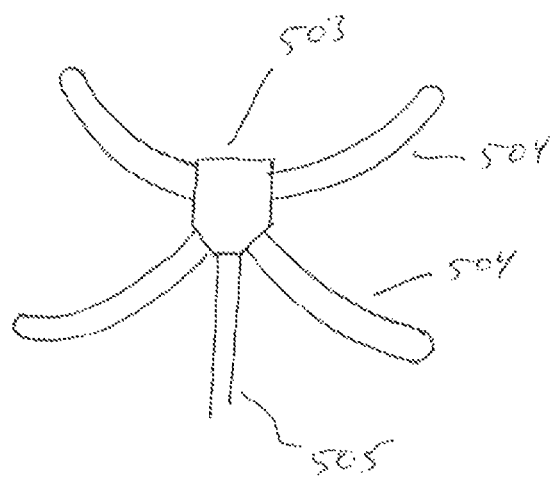

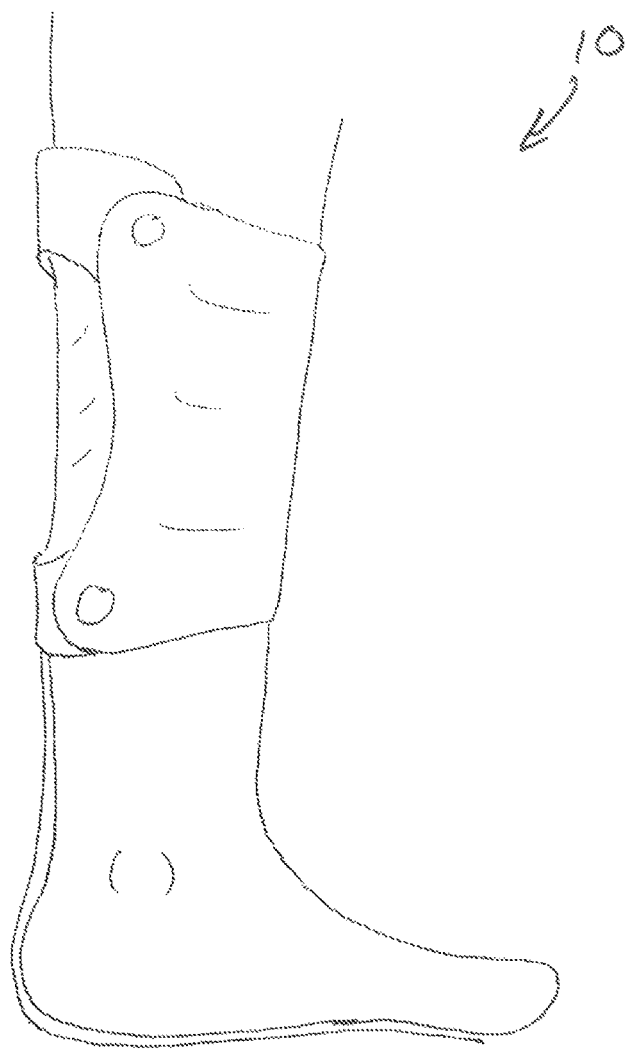

Figure 8:
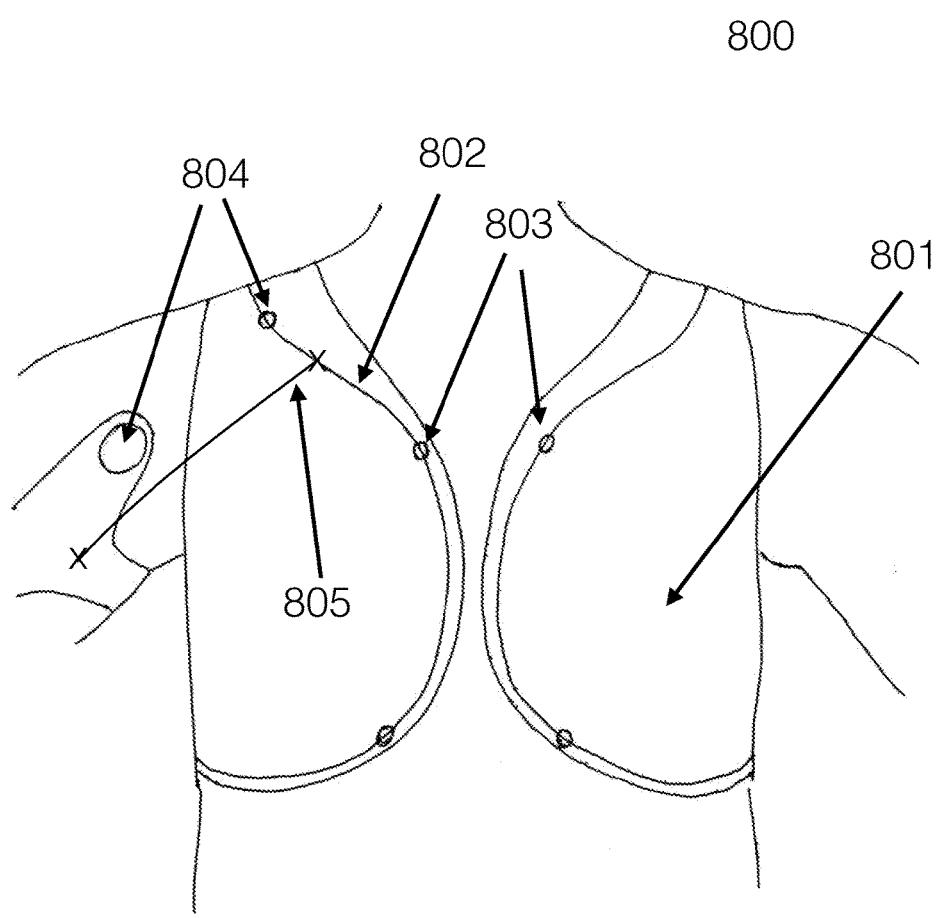

Prior Art - Figure 8 and Figure 9 Harnesses

Prior Art - Shoulder Disarticulation Socket Harnessing

COMPLIANT FORCE DISTRIBUTION SYSTEM

CROSS-REFERENCE TO RELATED APPLICATIONS

The present application is a continuation-in-part of U.S. Ser. No. 14/164,426, filed Jan. 27, 2014, currently pending, which claims priority to U.S. Provisional Ser. No. 61/849,509, filed on Jan. 28, 2013. Each of the applications listed above is hereby expressly incorporated herein by reference in their entirety.

BACKGROUND OF THE INVENTION

1. Field of the Invention

In general, the present invention is a system design and method for distributing external forces about the body using compliant means of force distribution. More in particular, the present invention is a means of fitting orthotics and prosthetics to users, to distribute device loads in a more comfortable and accommodating way.

2. Description of the Prior Art

For many years, various embodiments of man/machine interfaces have been explored and utilized. These interfaces have been required in various industries, ranging from backpacks to exoskeletal robotics to orthotics and prosthetics. Comfort, however, is one of the main limiting factors in man/machine interface designs. The human body is, by nature, dynamic. Our limbs and torso offer varying degrees of range of motion, our soft tissue offers compressibility and dynamically varying durometers, and the natural biomechanical movement of the human body is ever changing in shape and size through muscular excitation and long-term weight gain or loss. Conversely, man-made structures that encapsulate the dynamic body, are typically not dynamic. In many man/machine interface devices, foam padding is used to reduce point pressures on the body. Attachment systems often use foam backed straps or webbing around various limb and torso segments to attach the man/machine interface to the user. These straps tend to give high pressures over a relatively small surface area, decreasing comfort. Further, they tend to not completely inhibit movement between the body and the device, and in many cases actually promote movement between the two during the dynamic range of motion of the body.

In the field of backpack designs, foam padding is typically used to reduce the pressures of the interface to the body. While the foam padding effectively reduces the point pressures compared to a rigid member, there remains a limitation to the overall surface area that the forces can be dispersed among. Further, foam padding is typically bulking and heavy. In recent years certain backpack manufacturers, such as but not limited to the brand known by the trademark OSPREY has used a stretched mesh fabric over the back area of a backpack to further disperse the forces and load, and provide ventilation. While this may provide a lighter weight alternative to foam padding in these areas, their design offers limitations to the overall surface area that can be dispersed between. Further, their mesh design does not allow for inherent suspension of the load over the underlying anatomy in an optimal manner.

In the field of orthotics and prosthetics, suspension is typically achieved by suspending forces with rigid or semi-rigid elements. In clinical orthotics for instance, an ankle-foot orthotic typically uses a carbon fiber or plastic cuff with straps to maintain control and contact with the underlying anatomy. Because the body is dynamic in nature, both short term and long term, an interface form that is not inherently dynamic with the body is limiting.

There is an increasing need for man/machine interface systems in the field of robotics. As technology has progressed, exoskeletal robotic systems are on the brink of more widespread practical application. These systems may allow able bodied or physically challenged individuals to perform movements that they may otherwise not be able to perform, as the actuator elements of an exoskeletal system may augment much of the desired movements. In current exoskeletal applications, the man/machine interface methods used tend to rely on simple strap mechanisms for connectivity and suspension.

Whether in backpacks, orthotics, prosthetics, or robotic applications, the discomfort realized in man/machine interface systems stems from four core problems with existing interface designs. These may be the following:

1. Small surface area: The smaller the surface area that the given forces are spread among, the less comfortable for the user.

2. Sharp transitions: With conventional man/machine interface methods used, there tends to remain a relatively sudden change in pressures, going from high pressure to no pressure at the edge of the strap or interface mechanism. The sharper the transition leads to added discomfort and wear on the underlying anatomy.

3. Movement: Even slight shifting of the interface over the underlying anatomy (both movement over the skin surface and over the underlying bony and muscular structures alike) leads to discomfort as well as the perception of increased weight of the device.

4. Lack of control: Conventional interface designs typically do not effectively capture the underlying anatomy in a way as to capture biomechanical movement with efficiency. This results in inefficiencies and increased energy expenditure of the user.

New and improved methods of dispersing forces about the body, and improved attachment means between man/machine interfaces and the body are required. The preferred embodiment eliminates each of the above core challenges over existing man/machine interface designs. An extensive opportunity for design advancements and innovation remains where the prior art fails or is deficient.

SUMMARY OF THE INVENTION

The present invention relates generally to a novel man/machine interface system that reduces point pressures, and movement, and increases surface area, and control, creating a much more comfortable and efficient connectivity between man and machine. In particular, the present invention is a new and improved apparatus system and method for managing forces and comfort for prosthetics and orthotics users.

Torso Orthotic: The current invention may comprise a compliant fabric one piece member adapted for positioning around a user's torso below the shoulders having a left side panel, a middle panel, and a right side panel, wherein the left side panel is adapted to be worn around a user's left side and left front, the middle panel is adapted to be worn around a user's lower back, and the right panel is adapted to be worn around a user's right side and right front and wherein the left side panel and the right side panel are attachable in the front of user's torso. The invention may include an attachment point for suspending loads on said middle panel. It is to be understood that the one-piece member may include multiple pieces and that the construction may not be one piece. It is also understood that the invention may not necessarily be located under the shoulders, but may also incorporate a design that covers some and or portions of the shoulders.

Furthermore, the current invention may utilize a support system stabilizing unit adapted to integrate into the compliant fabric one-piece member wherein the perimeter of the left side panel, the perimeter of the middle panel, and the perimeter of the side panel are supported by a tubular or non-tubular support member. It is contemplated that the support member may consist generally of loops or portions of loops attached and integrated into the fabric member.

Such apparatus may generally be used for torso orthotic applications, wherein support of the torso may be desired, or for other such orthotic related functions.

Limb Orthotic Section: The limb orthotic section may comprise a section or sections of fabric, and may utilize a cable, or the like functionally, attached thereto, to effectively control the dynamic forces through the fabric. Such fabric section may be attached to the orthotic section, and be used as a connection between the user and the orthotic.

Exoskeletal Robotic interfaces: The exoskeletal robotics sections may comprise a section or sections of fabric, and may utilize cable, or the like functionally, attached thereto, to effectively control the dynamic forces through the fabric. Such fabric section may be attached to the exoskeletal robotics section, and be used as a connection between the user and the device.

Upper Extremity Harness Interface and Suspension:

The upper extremity harness interface and suspension section may comprise a micro-frame-stabilizing unit to capture mechanical control of bony structure about the limb segment, and may utilize fabric spanned there between to offer increased control and comfort. It may alternatively utilize a fabric section about the user's torso, similar to a vest, which may utilize cable, or the like functionally, to effectively control the dynamic forces through the fabric about the body. Such fabric section may be attached to the prosthetic section, and be used as a connection between the user and the device.

Conventional upper extremity suspension and control interfaces, often referred to as FIG. 8 and FIG. 9 harnesses, consist of relatively narrow webbing that wraps around and loops around the torso, often under the sound side axilla area. To help spread the forces, padding is sometimes attached to the webbing straps in the sound side axilla area. While this helps to ease the transitions of high force to no force at the edges of the webbing to help prevent roping and edge pressure, it does not minimize the amount of force per square inch. As a result, conventional FIG. 8 and FIG. 9 harnesses are typically very uncomfortable. Typical FIG. 8 and FIG. 9 harnesses also cause the user's shoulders to be pulled forward, which can be quite uncomfortable. And finally, conventional FIG. 8 and FIG. 9 harnesses offer limited control capabilities, as the harnesses do not hold secure in all body positions, such as when bending forward or reaching up.

Shoulder interface and suspension: The shoulder prosthetic interface section may comprise a micro-frame-stabilizing unit to capture mechanical control about the torso, and may utilize fabric spanned there between similar to a vest, to offer increased control and comfort. It may additionally utilize a fabric section about the user's torso, similar to a vest, which may utilize cable, or the like functionally, to effectively control the dynamic forces through the fabric about the body. Such fabric section may be attached to the prosthetic section, and be used as a connection between the user and the device.

Transfemoral interface: The transfemoral socket interface section may comprise at least one fabric section about the limb, which may utilize cable, or the like functionally, to effectively control the dynamic forces through the fabric about the body. Such fabric may span between or among biomechanical stabilizing units to effectively control tissue, and increase device comfort, and device control.

Transtibial interface: The transtibial socket interface section may comprise at least one fabric section about the limb, which may utilize cable, or the like functionally, to effectively control the dynamic forces through the fabric about the body. Such fabric may span between or among biomechanical stabilizing units to effectively control tissue, and increase device comfort, and device control.

Transhumeral interface: The transhumeral socket interface section may comprise at least one fabric section about the limb, which may utilize cable, or the like functionally, to effectively control the dynamic forces through the fabric about the body. Such fabric may span between or among biomechanical stabilizing units to effectively control tissue, and increase device comfort, and device control.

Transradial interface: The transradial socket interface section may comprise at least one fabric section about the limb, which may utilize cable, or the like functionally, to effectively control the dynamic forces through the fabric about the body. Such fabric may span between or among biomechanical stabilizing units to effectively control tissue, and increase device comfort, and device control.

Such methods and devices may allow a more comfortable and functional connection between the user and the device by better managing tissue and spreading loads more effectively, providing a more gradual force transition throughout the interface, provide a greater biomechanical lock about the body, and decrease movement between the device and its user.

In this respect, before explaining at least one embodiment of the invention in detail, it is to be understood that the invention is not limited in this application to the details of construction and to the arrangement of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting. As such, those skilled in the art will appreciate that the conception, upon which this disclosure is based, may readily be utilized as a basis for the designing of other structures, methods and systems for carrying out the several purposes of the present invention. It is important, therefore that the claims be regarded as including such equivalent constructions insofar as they do not depart from the spirit and scope of the present invention.

Accordingly, titles, headings, chapters name, classifications and overall segmentation of the application in general should not be construed as limiting. Such are provided for overall readability and not necessarily as literally defining text or material associated therewith.

Further, the purpose of the foregoing abstract is to enable the U.S. Patent and Trademark Office and the public generally, and especially the scientist, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved method of reducing point pressures of man/machine interfaces.

It is a further object of the present invention to provide a new and improved method of increasing the surface area of man/machine interfaces.

It is a further object of the present invention to provide a new and improved method of decreasing movement between the user and the interface.

It is a further object of the present invention to provide a new and improved method of increasing the control of the user with the interface.

It is a further object of the present invention to provide a new and improved method of increasing the efficiency of the user.

It is a further object of the present invention to provide a practical and robust method of connecting the user and the device.

It is a further object of the present invention to provide a man/machine interface that is lightweight.

It is a further object of the present invention to provide a man/machine interface that is user adjustable.

It is a further object of the present invention to provide a man/machine interface that is modular.

It is a further object of the present invention to provide a man/machine interface that is simple to fabricate and fit to the user.

It is a further object of the present invention to provide a man/machine interface that is less expensive to fabricate for the user.

It is a further object of the present invention to provide a man/machine interface that is cooler to wear.

It is a further object of the present invention to provide a man/machine interface that is more cosmetic than conventional interfaces.

It is a further object of the present invention to provide a man/machine interface that is self-adjustable for the user.

It is a further object of the present invention to provide a novel backpack interface.

It is a further object of the present invention to provide a novel orthotic interface.

It is a further object of the present invention to provide a novel prosthetic interface.

It is a further object of the present invention to provide a novel robotic interface.

It is a further object of the present invention to provide limb stabilization.

It is a further object of the present invention to provide a limb immobilization method.

Another object of the present invention is to provide a new and improved system, which provides some of the advantages of the prior art, while simultaneously overcoming some of the disadvantages normally associated therewith.

These together with other objects of the invention, along with the various features of novelty that characterize the invention, are pointed out with particularity in the claims annexed to and forming a part of this disclosure. For a better understanding of the invention, its operating advantages and the specific objects attained by its uses, reference would be had to the accompanying drawings and descriptive matter in which there are illustrated preferred embodiments of the invention.

BRIEF DESCRIPTION OF THE DRAWINGS, ILLUSTRATIONS, AND PICTURES

The invention will be better understood and objects other than those set forth above will become apparent when consideration is given to the following detailed description thereof. Such description makes reference to the annexed drawings, illustrations and pictures.

FIG. 1A generally illustrates a preferred embodiment of a compliant force distribution stabilizing unit for a backpack interface on a user.

Figure 1B:
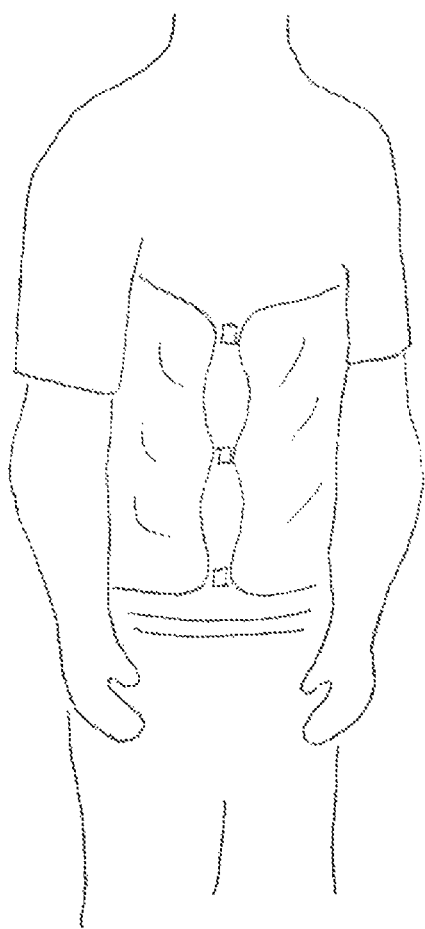

FIG. 1B generally illustrates a preferred embodiment depicting the front of the embodiment in FIG. 1A of a compliant force distribution stabilizing unit for a backpack interface on a user.

FIG. 2A generally illustrates a perspective view of an embodiment of a stabilizing unit.

FIG. 2B generally illustrates a perspective view of an embodiment of a stabilizing unit.

FIG. 3A generally illustrates an embodiment of a compliant connection means.

FIG. 3B generally illustrates an embodiment of a compliant connection means connecting two tubes.

Figure 4A:
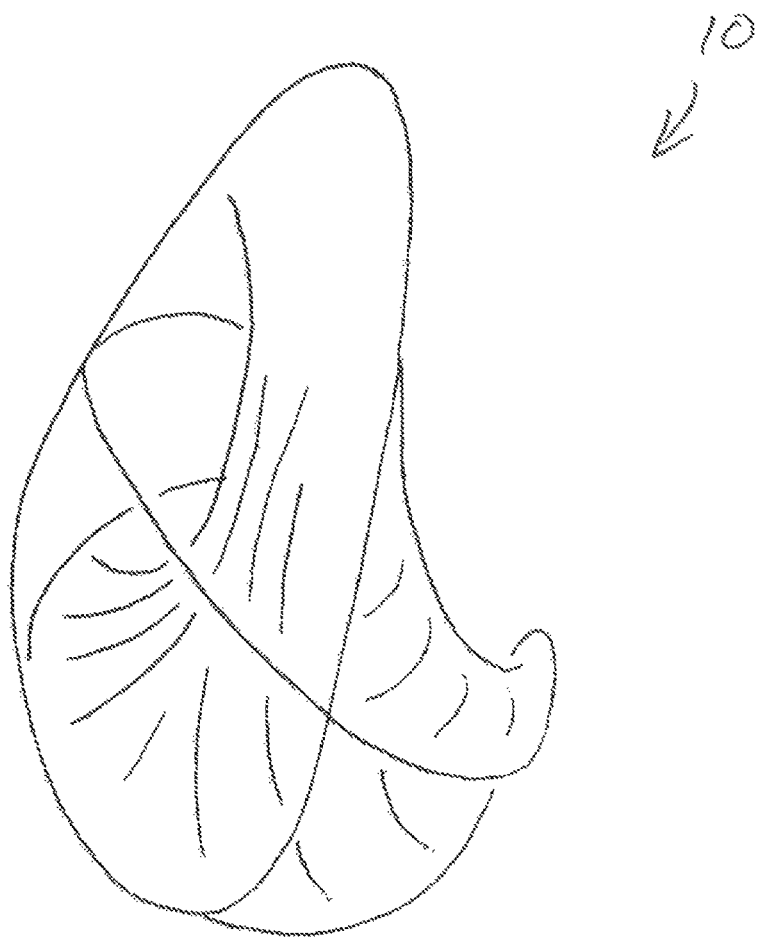

FIG. 4A generally illustrates a perspective view of compliant fabric stretched over an embodiment of a stabilizing unit for use around a waist and torso.

FIG. 4B generally illustrates a proximal perspective view of compliant fabric stretched over an embodiment of a stabilizing unit for use around a waist and torso.

FIG. 4C generally illustrates a perspective view of compliant fabric stretched over an embodiment of a stabilizing unit for use around a waist and torso.

Figure 4D:
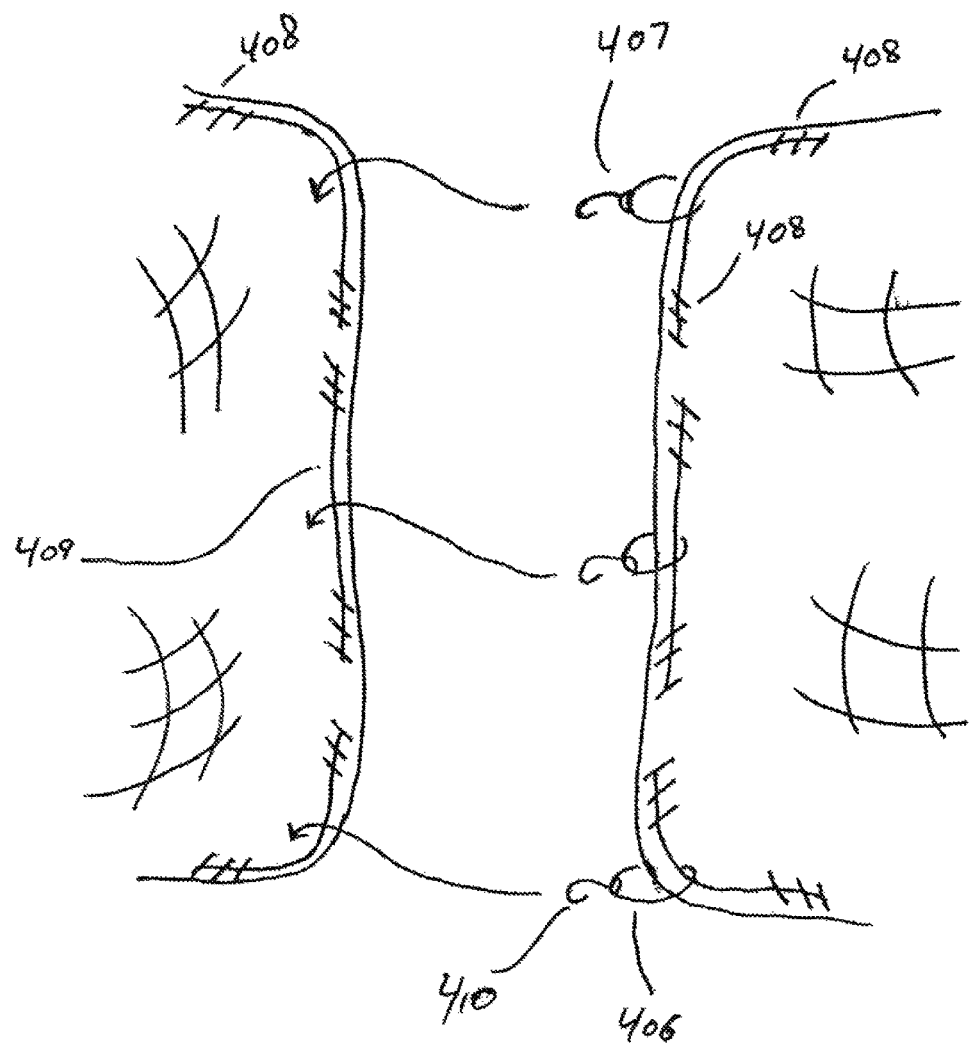

FIG. 4D generally illustrates a front view of fabric sections, which may extend around the users torso, and an embodiment of their attachment means and general locations.

FIG. 5A generally illustrates a pattern for stabilizing units as may be used around limb segments.

FIG. 5B generally illustrates modular stabilizing unit sections as may be used around limb segments, as viewed from the posterior.

Figure 6A:
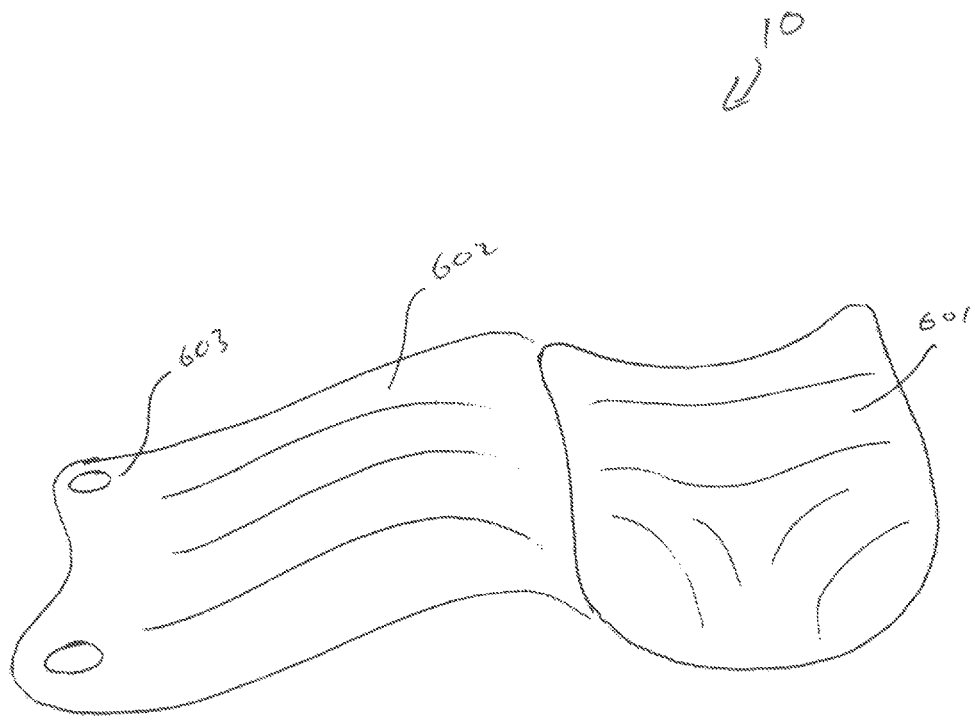

FIG. 6A generally illustrates a perspective view of compliant fabric wrapped around a stabilizing unit for use around a limb segment.

FIG. 6B generally illustrates a view of compliant fabric wrapped around a stabilizing unit around a limb.

Figure 7A:
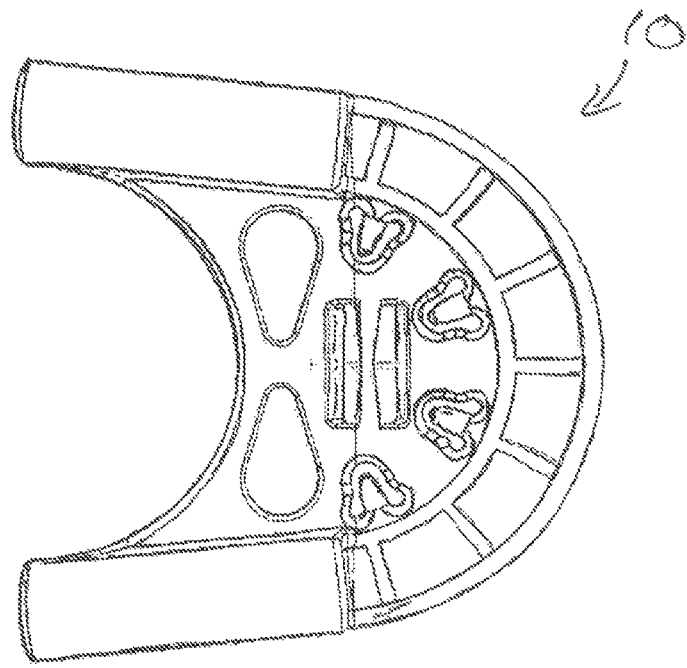

FIG. 7A generally illustrates an embodiment of a proximal attachment section for vertical stabilizing unit sections, as illustrated from the front view with the proximal end of the unit to the right.

Figure 7B:
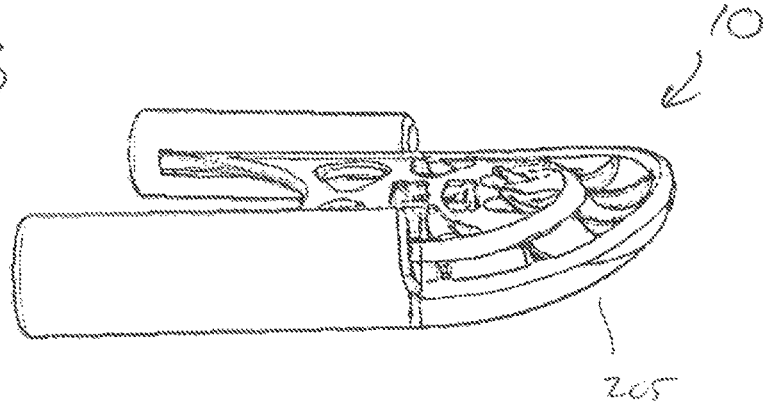

FIG. 7B generally illustrates an embodiment of a proximal attachment section for vertical stabilizing unit sections, as illustrated from the perspective side view, with the proximal end of the units to the right.

FIG. 8 generally illustrates an embodiment of an upper extremity control and suspension harness using compliant materials and broad force distribution.

Figure 9A:
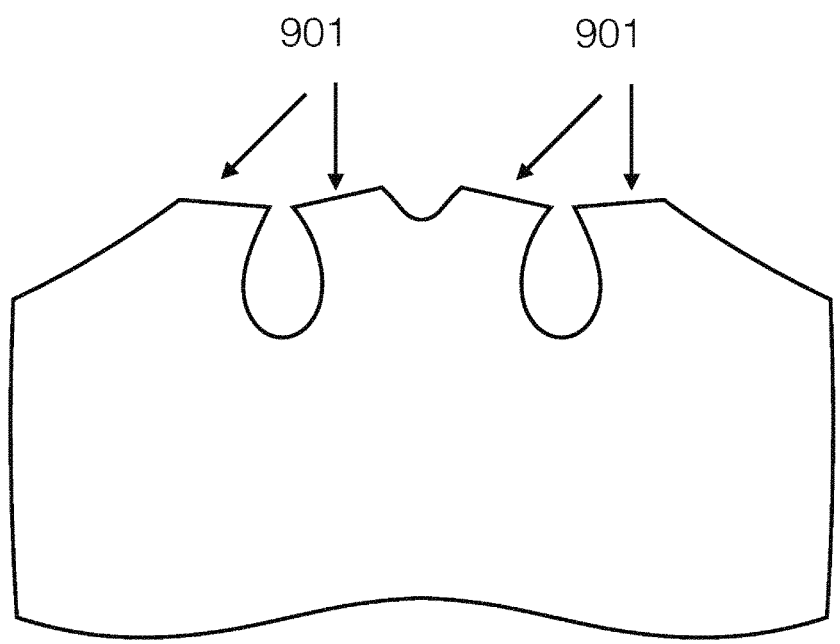

FIG. 9A generally illustrates a pattern for an upper extremity control and suspension harness using compliant materials and broad force distribution.

Figure 9B:
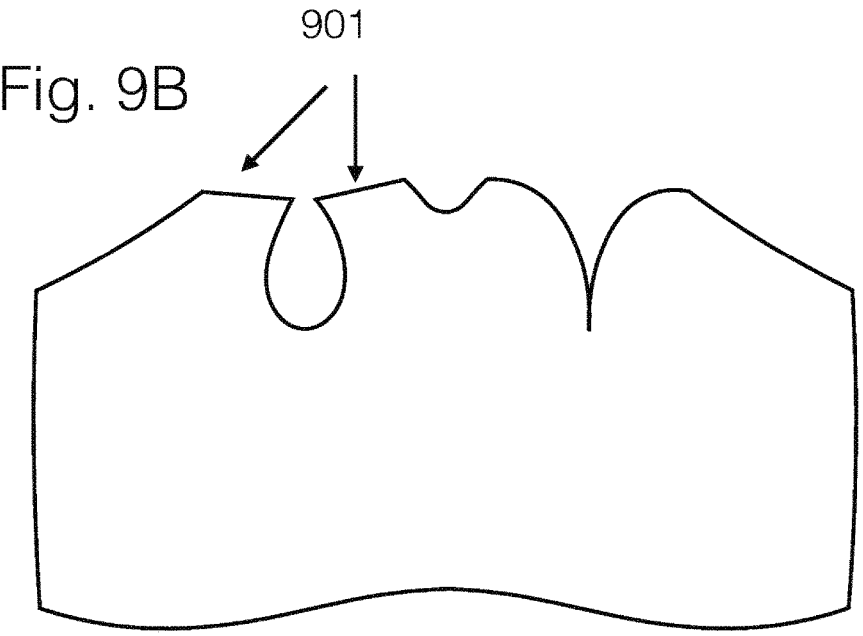

FIG. 9B generally illustrates a pattern for an upper extremity control and suspension harness for shoulder disarticulation prosthetic level fittings using compliant materials and broad force distribution.

Figure 10:
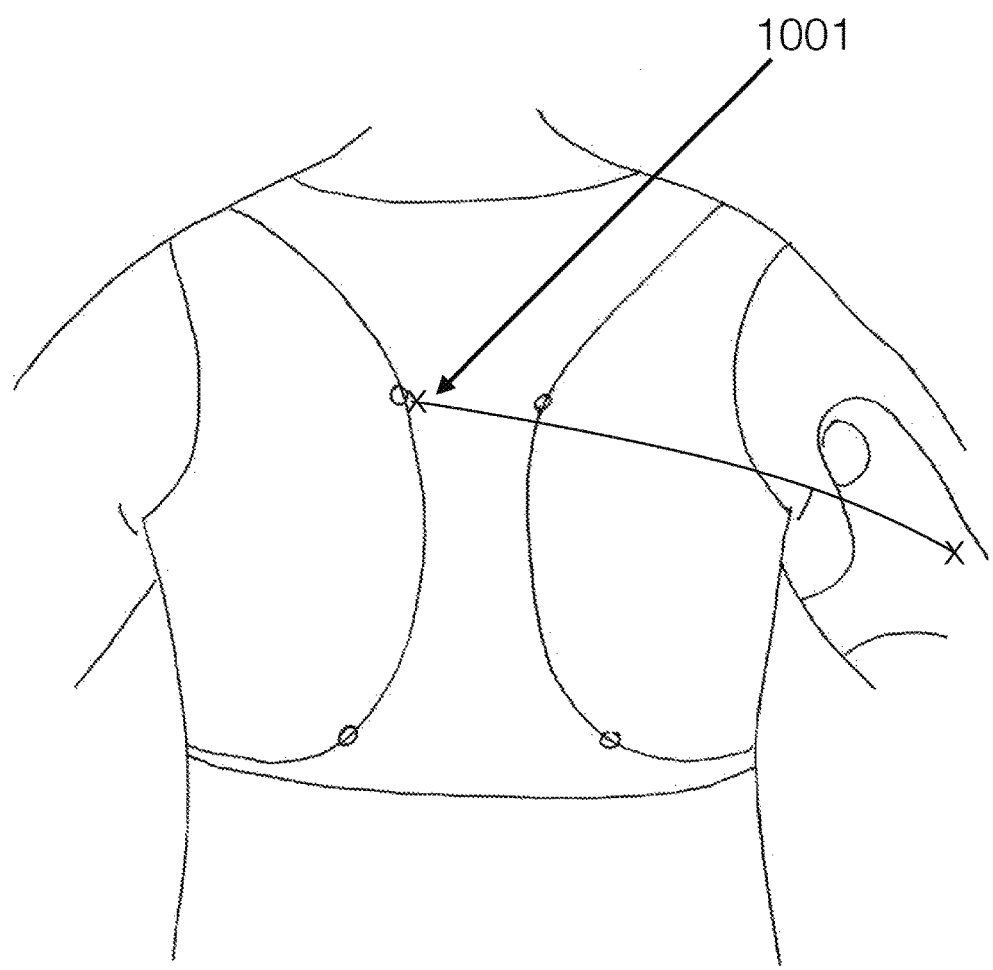

FIG. 10 generally illustrates the posterior view of an embodiment of an upper extremity control and suspension harness using compliant materials and broad force distribution, within integrated control strap.

Figure 11:
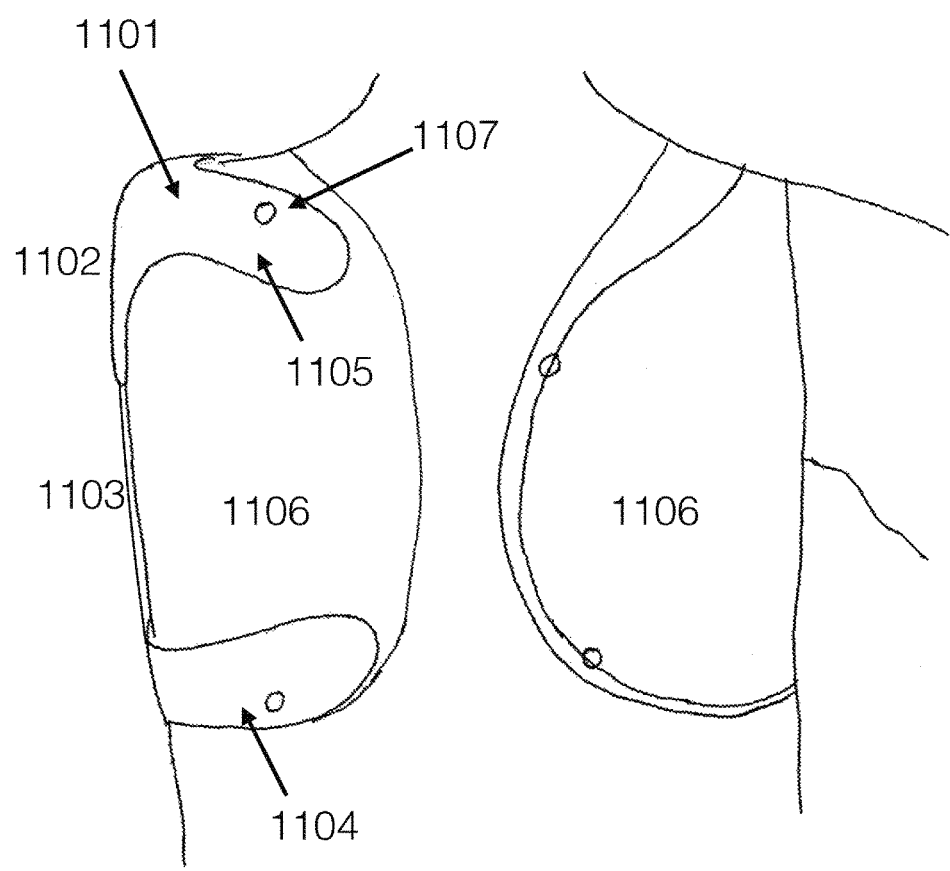

FIG. 11 generally illustrates an improved embodiment of an upper extremity control and suspension interface for shoulder disarticulation level fittings using compliant materials and broad force distribution.

Figure 12:
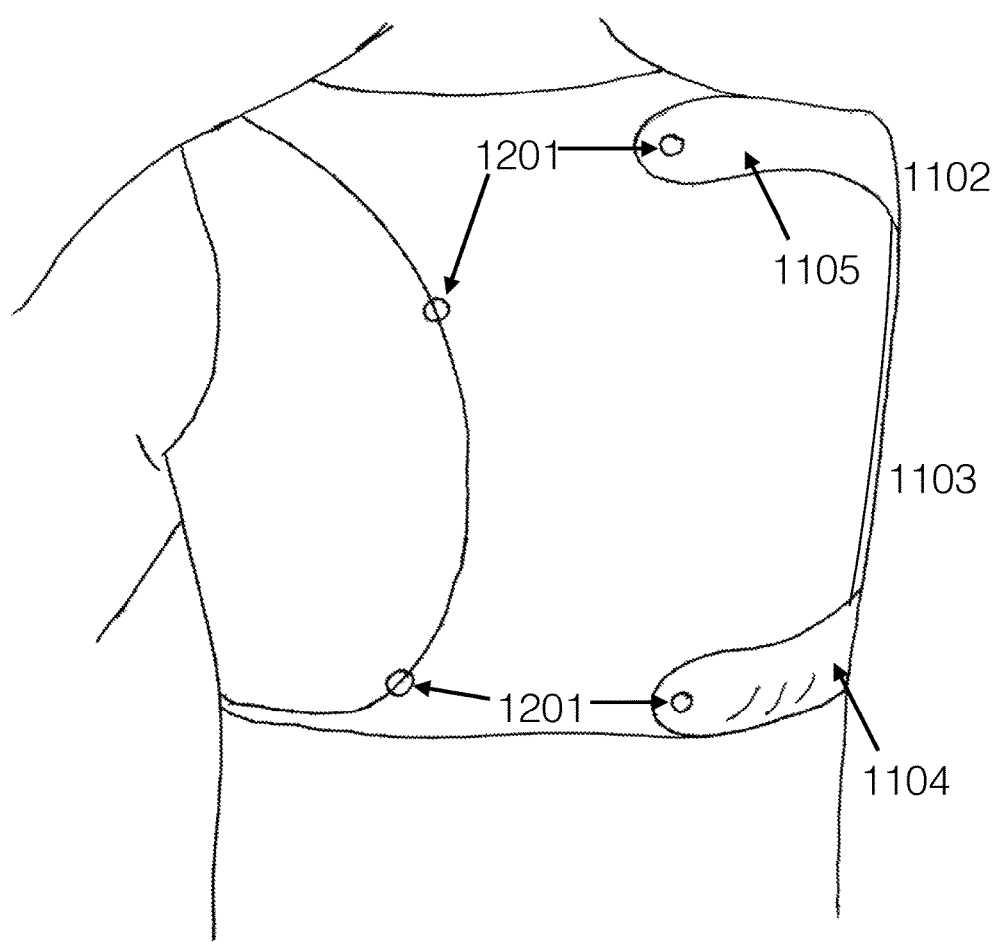

FIG. 12 generally illustrates a posterior view of an improved embodiment of an upper extremity control and suspension interface for shoulder disarticulation level fittings using compliant materials and broad force distribution.

Figure 13A:
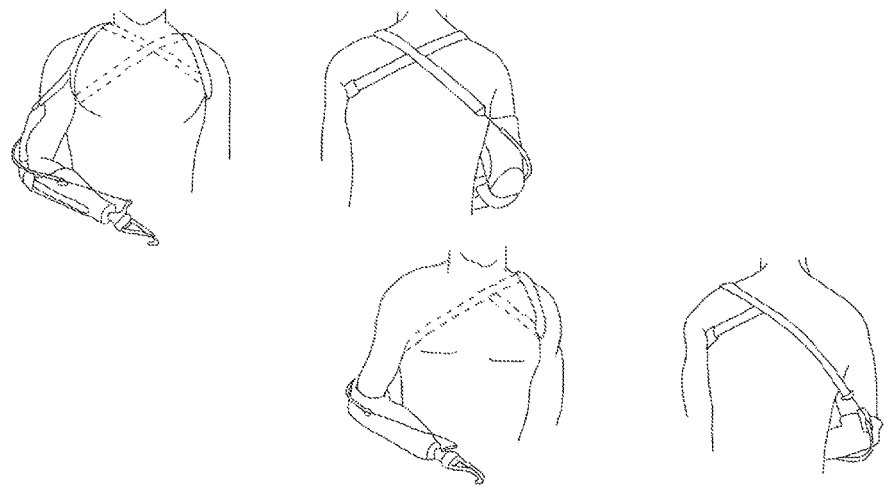

FIG. 13A generally illustrates prior art for FIG. 8 and FIG. 9 strap harnesses.

Figure 13B:
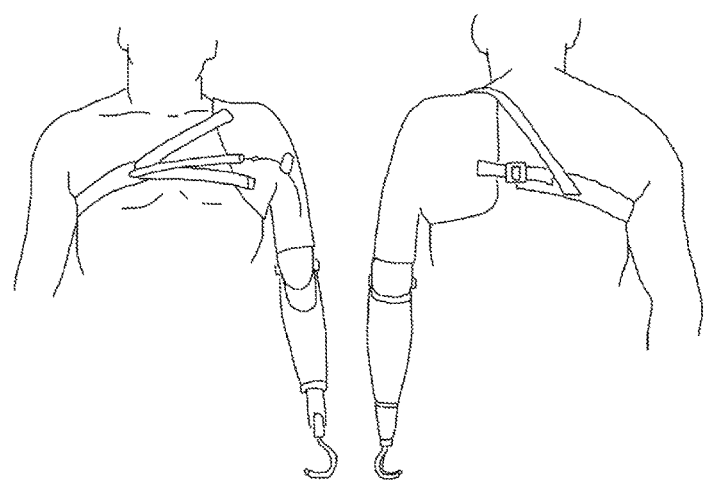

FIG. 13B generally illustrates prior art for shoulder disarticulation level fitting harnessing.

Figure 14:
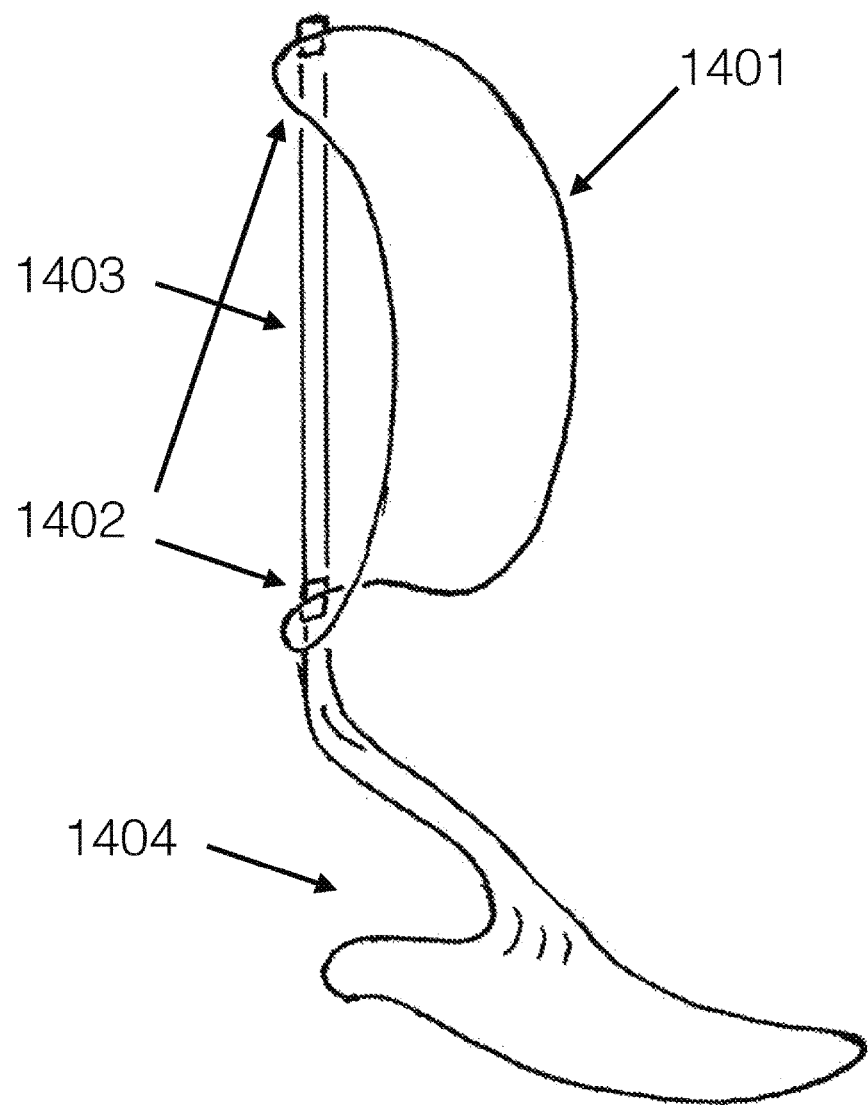

FIG. 14 generally illustrates an orthotic cuff using compliant materials and broad force distribution.

Figure 15A:
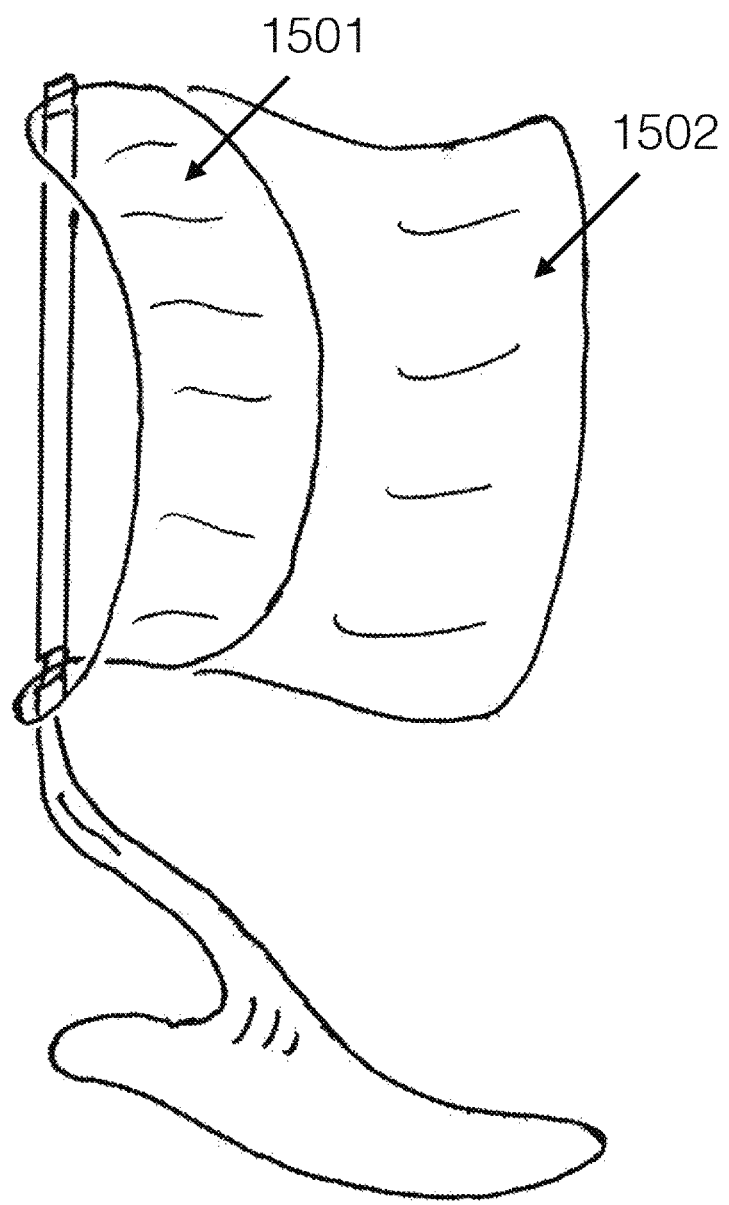

FIG. 15A generally illustrates an orthotic cuff using compliant materials and broad force distribution, with integrated fabric.

Figure 15B:
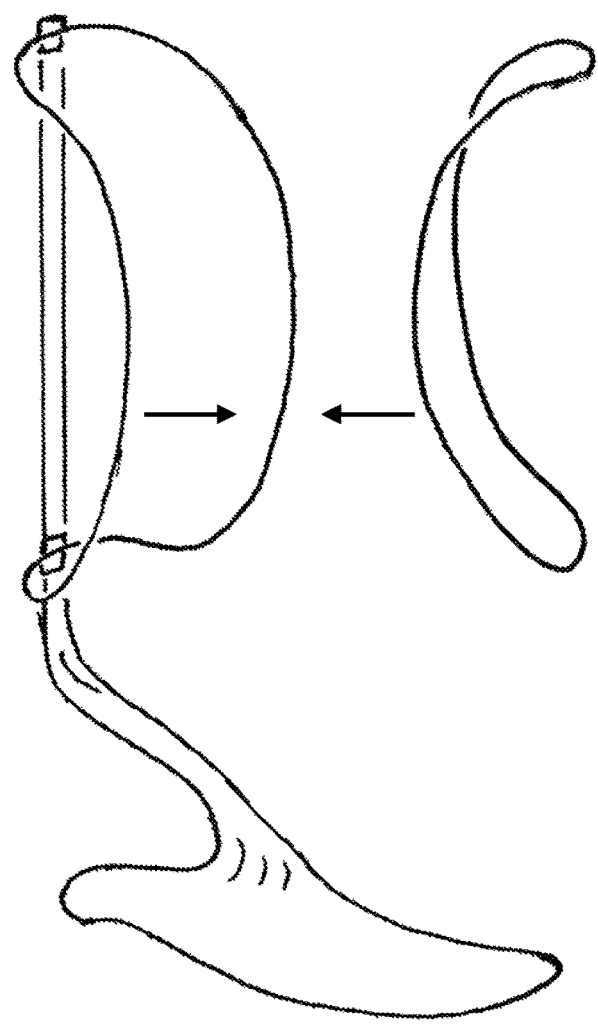

FIG. 15B generally illustrates an orthotic cuff using compliant materials and broad force distribution, using opposing panels to be connected together.

Figure 16:
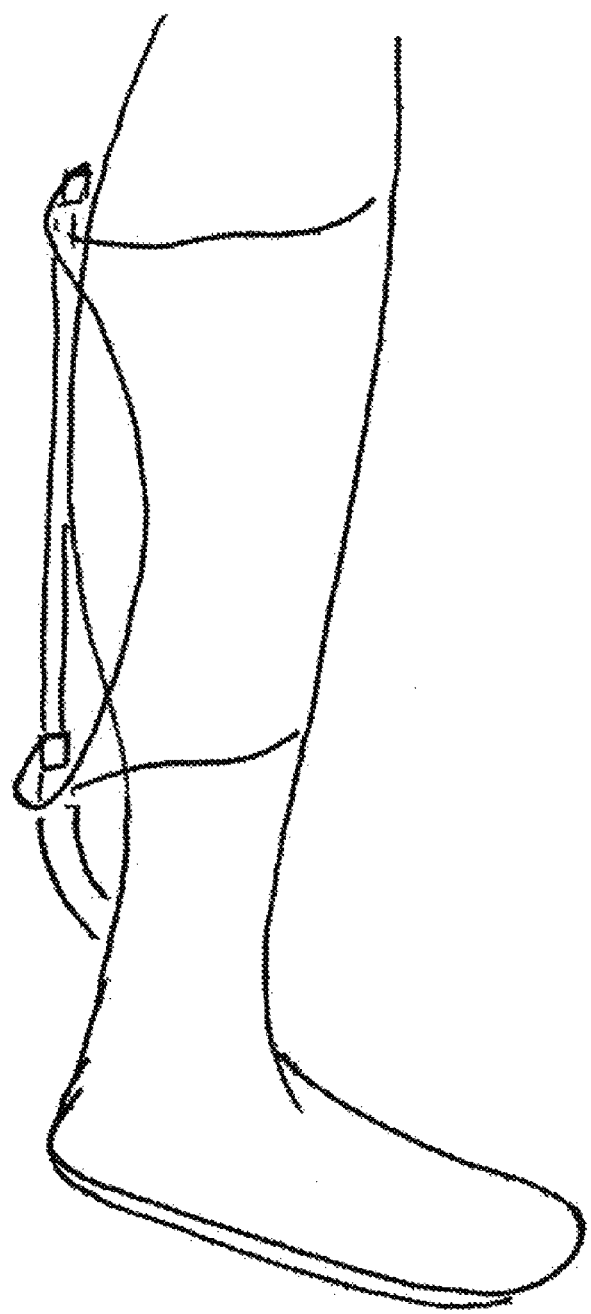

FIG. 16 generally illustrates an orthotic cuff using compliant materials and broad force distribution donned onto a limb segment.

Figure 17:
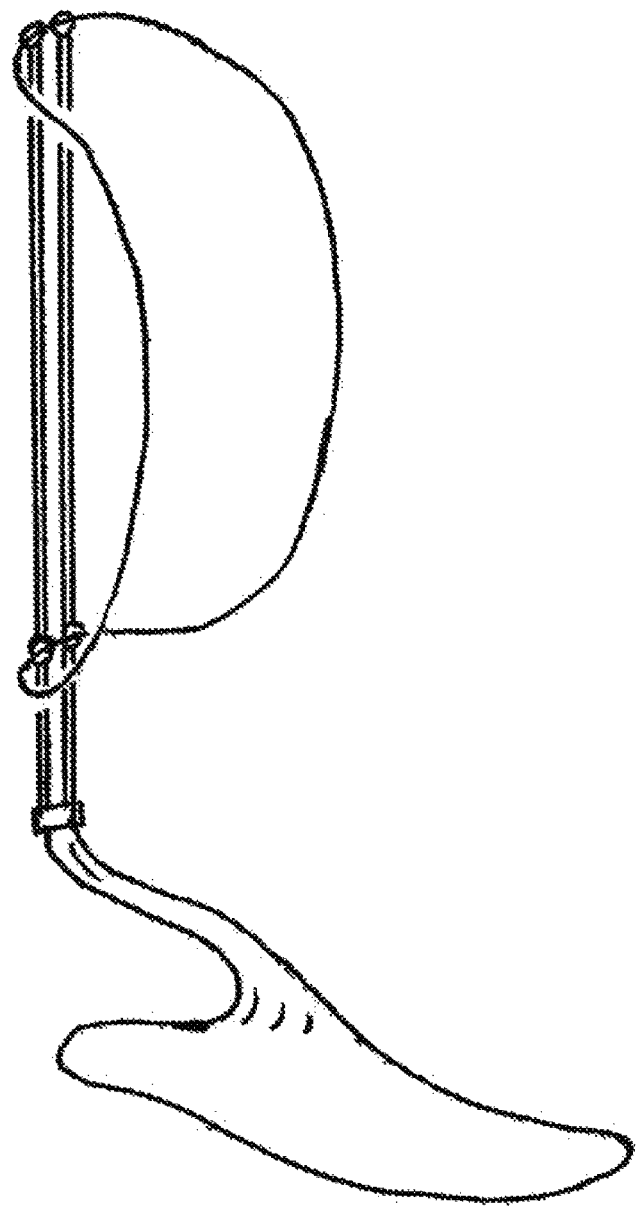

FIG. 17 generally illustrates an orthotic cuff using compliant materials and broad force distribution, with a modularly adjustable support structure.

Figure 18:
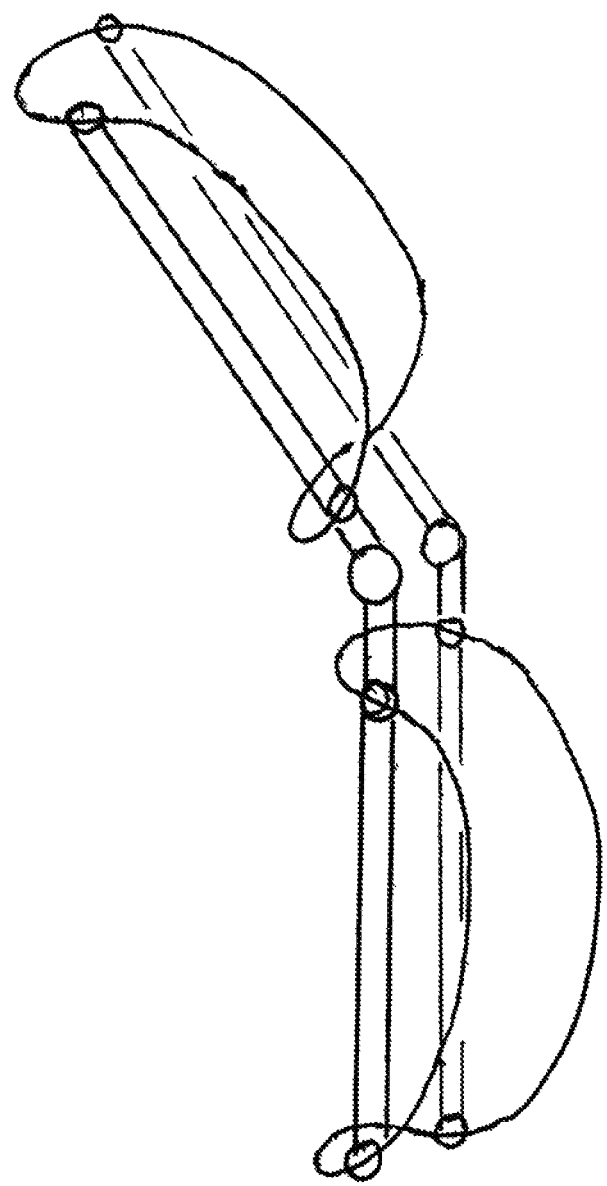

FIG. 18 generally illustrates an orthotic cuff using compliant materials and broad force distribution, for use as a knee brace.

Figure 19:
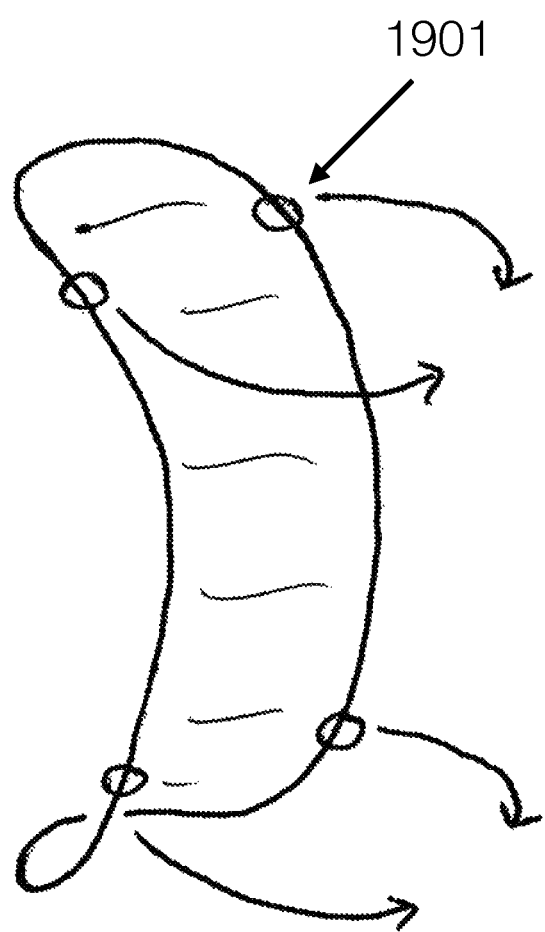

FIG. 19 generally illustrates a prosthetic cuff using compliant materials and broad force distribution, to span around a portion of a limb segment to control tissue and biomechanical lock.

DETAILED DESCRIPTION OF THE PREFERRED EMBODIMENTS

The current invention may be classified as a system, method, apparatus, and/or combinations thereof. The following detailed description does not define any aspect in a particular order of importance but rather attempts to organize the following for convenience only. Referring now to the drawings, wherein like reference numerals designate corresponding structure throughout the views, and by example, and amongst others, referring in particular to the figures, reference numeral 10 generally refers to a new and improved system, method, apparatus, and or combinations thereof hereinafter referred to collectively as invention 10 in accordance with a preferred embodiment. Other embodiments of such invention are also described herein. In a preferred embodiment, the current invention may include the following although it is contemplated that other combinations may be utilized as well as generally referred to in the application and illustrations described below.

As is illustrated in FIG. 1A and FIG. 1B, compliant force distribution techniques may be used to suspend loads around a user's torso. In such an example, a stabilizing unit 101 may be used to help hold orientation about the user 102, while a compliant fabric 103 may be used to suspend a predominant amount of the force about the user 102. It is contemplated that the stabilizing unit 101 and fabric 103 may each be fabricated from various types of materials, as well as in various embodiments. Further, the manner in which the compliant force distribution techniques may interact with the underlying body of the user 102 may be performed in various manners depending on the use-case or need requirements of the particular application.

FIGS. 2A and 2B generally illustrate embodiments of a perspective view of compliant force distribution stabilizing unit 101, which may interact around a user's 102 torso. In such examples, the stabilizing unit 101 may be fabricated of one or multiple components. FIGS. 2A and 2B illustrate separate components for the stabilizing unit 101 vertical element(s) or component(s) 201a and 201b, respectively and circumferential element(s) or component(s) 202a and 202b. In a preferred embodiment of such examples, the vertical components 201a and or 201b and circumferential components 202a and or 202b of the stabilizing unit 101 may be fabricated of tubing, such as aluminum, various metals, plastics, laminates, fiberglass, or any other material(s) known in the art of structural supporting elements. They may also be fabricated of non-tubing, in a sheet form, or other structural integrity shape to provide support in all directions, or in certain axis only. In a preferred embodiment, the vertical component 201a and or 201b may be relatively rigid in order to hold vertical support. Proximal end 205 of the vertical element 201a and or 201b may have a slight outward bend to provide additional comfort as it contours to the underlying anatomy of the user. One embodiment of which is illustrated in FIG. 7. The circumferential element 202a and or 202b may be relatively rigid to flexible. Flexibility of the circumferential element 202a and or 202b may be flexible in one or more axis, though in a preferred embodiment, the flexibility may be isolated to the axis in line with bending circumferentially around the user 102, and such flexibility may be managed to ensure that the structure holds the necessary amount of support to the structure as a whole. By doing so, the circumferential element 202a and or 202b may further support vertical loading within the device.

Elements 201a and or 201b or elements 202a and or 202b may be fabricated from tubing, wire, laminated material, plastic, fabric, spring steel, metals, adhesives, various fabrics, various layers of hook and loop type of material attached together, or any other material(s) which may assist in maintaining support in one or more directions. If elements 202a and or 202b have properties, which allow it to bend in the circumferential direction, but not bend along other axis, it may help further support the load of the system, in conjunction with the rest of the system.

The top to bottom width of element 202a and or 202b may be sufficient to allow the fabric section to contour effectively over the underlying anatomy of the user. Element 202a and or 202b may as well solely constitute a circumferential band around its distal end, and not the proximal end, as is illustrated in FIG. 2B. It may also be solely fabric based, and not utilize a physical stabilizing unit as shown.

It should be understood that the term circumferential should not be considered limiting. In a preferred embodiment, the circumferential element 202a and or 202b may wrap around the torso partially, fully, or any increment in between. In general, in a preferred embodiment, the circumferential element 202a and or 202b may generally have a curvature in a general direction around at least a portion of the user's torso.

The circumferential elements 202a and or 202b may be connected at their ends, as illustrated in FIG. 2A, or may not be connected. Their anterior connection point may use a molded piece that may accommodate additional accessories or functions, such as strap supports or connection points for other elements.

The vertical elements 201a and or 201b and circumferential elements 202a and or 202b may be connected to connection area(s), point(s) and or joint(s) 203 in a manner in which they have a rigid connectivity, or may be connected in a manner in which the connection points 203 are compliant. They may also be connected in a manner in which the connection points 203 are adjustable. Various areas of the elements 202a and or 202b may have flexible characteristics, while other areas may be more rigid in order to promote bending of the element 202a and or 202b in certain areas more than others.

Circumferential element 202a and or 202b may alternatively use a combination of tubing with material on its inside to help promote stability in certain directions. In such an example, such a material may be applied to its inner cavity, which may harden the tube into a certain shape. That tube may then provide characteristics of form and function in a manner consistent with the required outcomes for stability of the system around the user. Furthermore, additional structural elements such as spring steel or other such materials may be applied into the tube with or without bonding agents. The combination of various materials, such as by way of example, spring steel inside of plastic tubing may allow for the capture of bendability in certain directions, but not others, as the unit 101 wraps circumferentially about a user's torso or waist.

FIG. 3A illustrates one embodiment of compliant connectivity between vertical elements 201a and or 201b and circumferential elements 202a and or 202b. In such an example, a material or fabric 300 may have hook and loop type surfaces on either side, allowing for section 301 for instance to wrap around pole, tube or structure 305 to its right. The hook and loop surfaces may then allow for the material 300 to adhere to itself, thereby making a connection point around pole or tube 305. Section 302 may accomplish the same as it wraps around pole, tube or structure 306 in the downward direction, as illustrated in the image. Sections 303 and 304 may do the same. FIG. 3B illustrates one example of the hook and loop material that may wrap around the two crossing tubes 305 and 306, connecting them together at point 309. In such an example, holes 307 become the corners of the central point of connection. Cuts 308 then become the inside edge of the four bands that wrap around the tubes 305 and 306. In such an example, an area of the material generally along the connection point locations, such as the areas around and under where the tubes 305 and 306 may cross, may be further supported and strengthened with another type of stronger material attached thereto to increase durability.

The compliant material 300 may also connect to the underlying structures 305 and 306 using similar hook and loop materials. In such an example, loop material may be attached to the structure 305, which may mate to the material 300, whose surface may have a hook face. This may also allow for elements 201a and or 201b and 202a and or 202b to connect in an adjustable manner. By the connectors being modular, they may be disjoined, and then rejoined at various locations. They may also allow for element 202a and or 202b to be adjustable in width, causing the connection points 203 to need to be adjusted to accommodate such adjustability. In such an example, the width of element 202a and or 202b may be adjusted to accommodate various sized individuals who may wrap element 202a and or 202b around their waist. This adjustability may be in the lateral direction, in the circumferential direction, in the length of the arm elements 202a and or 202b, in the curvature, or any other direction. Likewise, element 201a and or 201b may be adjusted in height or other dimensions. For instance, area 204 may be used to provide adjustability of the elements 202a and or 202b, allowing them to slide within, over, or among each other to alter the length or dimensions of elements 202a and or 202b.

The elements 202a and or 202b may also provide enough flexibility in certain directions to allow them to fold to make it easier for storing. If tube sections are used for the stabilizing unit 101, they may be able to be disconnected from one another similar to how tent poles may be disjoined and rejoined together, and may further use shock cord to maintain their proximity upon disjoining them.

By allowing the stabilizing unit 101 to becoming disconnected at various regions of the device, such as but not limited to specifically areas 203, or other areas along the length of the element 202a and or 202b, this may allow for the compliant fabric 300 to more easily be disconnected from the stabilizing unit 101 and swapped out for another compliant fabric piece. The use of interchangeable fabric sections on the device may allow for customization in color, repair, or other factors of user preference in look, feel, or other characteristics.

The distal attachment of area 203 may likewise use a compliant structure to support the connectivity at such location. In one embodiment, area 203 may be disjoined to assist in donning the fabric 300 over the stabilizing unit 101. Once disjoined, it may be easier to stretch the tight fabric 300 over the stabilizing unit 101, and then utilize the leverage created by the disjoining of the various stabilizing unit 101 components at area 203 to leverage them back together, thus stretching the fabric 300 tighter than may be able to be done otherwise.

Using compliant structures may have advantages over more rigid parts, as the compliant nature of the connector may allow for added durability.

Conversely, alternative conventional attachment means may be used to connect the vertical elements 201a and or 201b and circumferential elements 202a and or 202b together, such as plastic, metal, or other material based connectors. In such an example, a part may be formed with attachment points for, by way of example, tubes for elements 201a and or 201b and 202a and or 202b to integrate into, thus creating a rigid or semi-rigid joint connection. Additional components may be used, such as pins, clips, or other methods commonly used for connectivity, to secure the elements 201a and or 201b and 202a and or 202b into the joint. Likewise, the inherent force of the fabric section may hold elements 201a and or 201b and 202a and or 202b into the joint 203. Joint 203 may also be utilized for additional functionality, such as a connection point for the fabric, cords, or other. In general, elements 202a and or 202b may be used to assist in stretching compliant fabric 300 around the torso, in order to contour over the underlying anatomy, and assist in holding the device to the user.

FIG. 4A shows one embodiment of compliant fabric stretched over the underlying stabilizing unit. In such an example, the fabric may be stretched in a manner in which the curvature of the fabric material provides compliant force distribution over the underlying anatomy. In such an example, the stabilizing unit may or may not ever come in contact with the user, as the compliant fabric may bridge the span in between the various elements of the stabilizing unit, allowing for the compliant fabric to provide a biomechanically contoured hammock to the user.

FIG. 4B illustrates a perspective view from the anterior proximal end of the embodiment looking distal. As can be seen in the illustration, the compliant fabric may be spanned in between the stabilizing unit frame in a manner in which upon donning of the device, areas 401 may compress against the user's lateral sides, locking the device over the iliac crest and soft tissue areas. This may be used to support the device over the user. As areas 401 are compressed, it may inherently cause area 402 to move anterior, thereby providing additional support over the lower lumbar area of the back.

FIG. 4C illustrates an embodiment whereas the stabilizing unit 101 encompasses distal circumferential elements 202*b*, vertical elements 201*a* and proximal and distal attachment points 204 and 203 respectively. The compliant force distribution fabric 103 stretched around stabilizing unit 101, in such an example, may as well provide anatomically specific loading over the hip area of the user, as well as lumbar areas, and others, though may also have enough material to wrap circumferentially around the user's torso, partially or fully. In such an example, the stabilizing unit 101 circumferential elements 202*a* and or 202*b* may terminate at a fixed point 405, though the compliant fabric 103 may continue to extend past that point. Conversely, the fabric 103 may also terminate at or near the termination of the stabilizing unit 101. In either case, the termination end point 405 of the stabilizing unit 101 may be used as an anchor point for the fabric 103. If such fabric 103 extends, there may be additional connectivity points 406 and 407, or others in between, outside of, or in addition to, which may be used to connect opposing sides of the fabric 103 around the user.

Such attachment means may utilize conventional buckles, clips, or the like, or may utilize other more compliant means such as but not limited to cords sewn into or connected to the fabric, which may integrate with hooks on the opposing side, as is illustrated in FIG. 4D. The term hooks should not be considered limiting, as that may refer to any number of methods of physically connecting to, around, or amongst a cord. By way of example, if a cord were integrated into the fabric, by being affixedly sewn connected to area 408, or non-affixedly wound through area 409, and then that cord were snagged over a loop or hook 410 to physically grab the cord, then the force may be distributed through a broad area of fabric, minimizing the amount of force in an isolated area, thereby increasing durability.

Additional accessory attachment means may be included, such as location 411, where a shoulder strap may be attached, not shown. The opposing side of that strap may attach at or near point 407 on the anterior side of the body, by way of example. In such a case, a shoulder strap may be used for augmented or additional support of the load carried on the pack, not shown. The pack may be connected to the stabilizing unit.

The compliant fabric may connect to the stabilizing unit in a manner such as but not limited to: sewing a channel, VELCRO, attachment points, clips, snaps, hooks, loops, pockets or any other attachment means known in the art of connecting fabric to structures. In one embodiment, pockets may be sewn into the compliant fabric in areas 403 or also areas 404 to allow the compliant fabric to slide over the stabilizing unit in those areas, to assist holding such compliant fabric onto the stabilizing unit. In a preferred embodiment, such pockets on the compliant fabric may have hook or loop sewn into them to allow for other accessories to be connected to them in those areas 403 and or 404, such as but not limited to a backpack.

Still further, the compliant fabric may not be joined directly to the stabilizing unit in areas 404, thereby allowing it to be pulled tighter around the user in areas 404 to allow the stretch of the compliant fabric to contour to the user in a more user specific manner.

The stabilizing unit 101, or other areas of the compliant fabric and/or stabilizing unit 101, or combination thereof, may attach to other accessories or devices. For instance, the stabilizing unit 101 may connect to an exoskeletal robotic, or orthotic or prosthetic device, or other device, to connect the man and device. Alternatively, the unit 101 may connect to a modular backpack in order to allow for a load to be carried on the device. Such backpack may be modularly connected or disconnected using means known in the art of connecting devices together, such as but not limited to snaps, VELCRO, loops, tabs, buttons, or any other means known in the art of connection.

Such backpack design may be modularly swapped out for other backpack designs, or other designs used for specific functionality. For instance, a user may have their customizable fitted stabilizing unit with compliant fabric and disconnect their school backpack from it, and reconnect their hiking backpack to it. This would allow for a modular use of the system.

Still further, the device lends itself to having other accessories modularly attached to the system, such as water bottle holder, additional compartments, and other such devices or tools. Such accessories may be connected to the stabilizing unit and/or the compliant fabric in various sections.

In a preferred embodiment, such a device may not require the use of shoulder straps to maintain a secure load to the user. In conventional backpack designs, shoulder straps are the main load bearing areas to maintain the load off the user's body. Even though some backpacks offer waist straps, the shoulder straps remain an integral element of their functionality. However, in this preferred embodiment, the load may be maintained over and around the users waist and torso, but not require the use of shoulder straps. The use of a chest strap may be found to be beneficial however, to prevent the load attached to the unit from tending to fall posterior from the user. Modular chest straps may be used, which may be adjustable in various directions. Similarly, the compliant fabric itself may be spanned around the user's torso and connected toward the user's front. Such chest strap may be integrated within the remaining compliant fabric, or may be connected directly to a cross bar assembly (not illustrated), which may connect directly to the stabilizing unit. Such cross bar assembly may allow for the chest strap location to be isolated at the correct height, as well as allow the chest strap connection point to directed directly posteriorly, versus at an angle posterior and medial, reducing flexibility within the system, and increasing biomechanical lock about the user. In general, the more surface area of the user that has the compliant fabric stretched around them may allow for added load to be taken up, thereby reducing the amount of load per surface area unit of measurement.

Through taking advantage of the modularity of the proposed design, the chest straps may alternatively be modularly adjusted to be able to be used as shoulder straps instead. Likewise, it may be able to be disconnected and reconfigured such that it may function as a cross-chest strap from over the top of one shoulder to a distal attachment point across the body. In any such embodiment, the system as a whole may take up the forces about the torso, relieving load from being bore over the tops of the shoulders.

Similar means of dispersing forces about the user's body may be found in alternative segments of the body. By way of example, thigh or shin cuffs may be fabricated using the same compliant force distribution technology and methods. In such an example, a stabilizing unit 501 and 502 for a shin and thigh cuff respectively may be used, as illustrated in FIG. 5A in a flat pattern. Such stabilizing units may be positioned in a relative arc to roughly contour to the underlying anatomy of the user. Stabilizing units 501 and 502 may be specifically contoured in pattern to taper to the general shape of the underlying limb. By way of example, FIG. 5A unit 502 generally illustrates a thigh cuff pattern with its distal end facing up in the illustration. Such a piece may utilize a slight curvature toward its distal end as it sits on the limb, in order to allow for added knee flexion. Additionally, the lateral aspect of such cuff, as is shown on the left side in the illustration, may have a slightly longer length than the medial side, in order to prevent interference as the leg moves through its range of motion.

The stabilizing unit may use a generally broad surface such as plastic, laminate, fiberglass, or other materials known in the art, or may use tubing, fabric, or other materials. It may be pre-formed into a general arc shape, or may utilize its own compliant properties to bend it in conjunction with the pull from the compliant fabric, to give it a general arc shape to contour around the user. Whatever the configuration of the stabilizing unit may be, it may effectively function as a hammock stand, and the compliant fabric may function as the hammock, spreading the forces over a broad surface area.

FIG. 5B illustrates a similar function as FIG. 5A, though through using tube sections extending from a relative central region, versus around the perimeter as in FIG. 5A, or the functionally equivalent, to span the compliant fabric around the user. In FIG. 5B, the connector piece 503 may allow for the tube sections 504 to connect together. This assembly may then be connected to a tube section 505 that may attach to the remainder of an ankle foot orthosis, knee brace, or the like. Its attachment location(s) may be customized according to the anchoring needs for the brace section. The term tube should not be considered limiting as it is simply illustrating a physical structure for stretching the compliant fabric between. These tubes 504 and 505 may come in various modular sizes, or may be customized for each user. Their rotation, angulation, and circumference may all be customizable characteristics. Similar to what is shown in FIG. 5A, the compliant fabric may be stretched around the tubes in FIG. 5B. FIG. 6A and FIG. 6B generally illustrate one embodiment of compliant fabric stretched over the stabilizing unit of a limb cuff. Compliant fabric 601 may be generally stretched over the stabilizing unit, and may be attached to its outside, or may wrap around the outside of the stabilizing unit and attach on its inside. By attaching the compliant fabric around the stabilizing unit, the line of pull may generally be in shear, providing unique opportunities for attachment by changing the direction of force about the system. For instance, the compliant fabric 601 may be attached via hook, loop, glue, buttons, snaps, zippers, sewn, or any other methods used in the art. If a disjoinable attachment method may be used, it would allow for the compliant fabric to be removed for cleaning and other such purposes.

Compliant fabric section 602 may be attached to the compliant fabric 601 or to the stabilizing unit, and may have secondary attachment means 603, which may allow compliant fabric section 602 to wrap around the limb, and attach to the contralateral side of the cuff. Either attachment means may be user adjustable to allow for the cuff to be more specifically sized to the user. Additionally, the compliant fabric 601 may as well be user adjustable as it attaches to the stabilizing unit to allow for its tightness to be adjusted.

In general, in such an example as discussed through this disclosure of using compliant force distribution technology and means, increasing the surface area of the compliant fabric may be beneficial in order to allow for the forces to be spread over a broader area. In such an example, the entire surface in contact with the user may generally be compliant fabric, and under stretch when donned by the user, no foam padding, struts, or other members may be in contact with the user, except for compliant fabric.

Such fabric may be a solid fabric, or a mesh. It may also be elastic or non-elastic in nature. In a preferred embodiment, the compliant fabric may be mesh to provide lightweight, breathable, and durable characteristics. Further, the fabric may be stretched toward the end range of its elasticity, thereby maintaining the volumetric size as it wraps around the user. Using a mesh fabric may also allow for the fibers to not have elasticity, but the fabric to retain stretch through the geometric shape of the mesh elongating, such as a diamond shape which may elongate in a direction giving the perception of stretch.

It is therefore contemplated the current invention may comprise an embodiment of a compliant force distribution system to suspend loads around a user's torso below the shoulders comprising: a compliant fabric one piece member adapted for positioning around said user's torso below the shoulders having a left side panel, a middle panel, and a right side panel, wherein said left side panel is adapted to be worn around a user's left side and left front, said middle panel is adapted to be worn around a user's lower back, and said right panel is adapted to be worn around a user's right side and right front and wherein said left side panel and said right side panel are attachable in the front of user's torso; and an attachment point for suspending said loads on said middle panel.

It is also contemplated that the current invention may further include a support system stabilizing unit adapted to integrate into said compliant fabric one piece member wherein the perimeter of said a left side panel, the perimeter of said middle panel, and the perimeter of said side panel are supported by a tubular or structural member system, which may include flexible structure elements.

It is also contemplated that the current invention may utilize a compliant fabric one piece member that is made from a compliant mesh fabric; wherein said tubular support system comprises a first loop and a second loop wherein said first loop and said second loop are connected; wherein said first loop and said second loop are made from aluminum; wherein said attachment point is connected to said support system stabilizing unit; wherein said middle panel further include an integrated cavity for placing items; wherein said left side panel and or said right side panel further include an integrated cavity for placing items. Still furthermore, the current invention may utilize for an attachment point for suspending said loads, a vertical support connected to said middle panel.

Torso Orthotic:

Similarly to the prior backpack design, the use of compliant fabric mesh spanned between stabilizing unit elements provides an effective man/machine interface to control forces more effectively. Expanded use-case applications may encompass clinical orthotics and prosthetics.

The current invention may comprise a compliant fabric one piece member adapted for positioning around a user's torso below the shoulders having a left side panel, a middle panel, and a right side panel, wherein the left side panel is adapted to be worn around a user's left side and left front, the middle panel is adapted to be worn around a user's lower back, and the right panel is adapted to be worn around a user's right side and right front and wherein the left side panel and the right side panel are attachable in the front of user's torso. The invention may include an attachment point for suspending loads on said middle panel. It is to be understood that the one-piece member may include multiple pieces and that the construction may not be one piece. It is also understood that the invention may not necessarily be located under the shoulders, but may also incorporate a design that covers some and or portions of the shoulders.

Furthermore, the current invention may utilize a support system stabilizing unit adapted to integrate into the compliant fabric one-piece member wherein the perimeter of the left side panel, the perimeter of the middle panel, and the perimeter of the side panel are supported by a tubular or non tubular support member. It is contemplated that the support member may consist generally of loops or portions of loops attached and integrated into the fabric member.

Such apparatus may generally be used for torso orthotic applications, wherein support of the torso may be desired, or for other such orthotic related functions. In such a use-case, the fabric sections in coordination with the structural elements may generally support the torso in such as away as to provide the desired outcomes for clinical orthotics use, such as but not limited to scoliosis related issues.

The fabric section may be modularly adjustable such that upon donning the system, the user may be able to self adjust the device to achieve the desired tightness, control, and support about the body. Utilizing such a design may provide a practical cost effective solution for such users. Conventional orthotic braces are heavy, bulky, hot, and require comparatively expensive materials and fabrication processes to fit to a user. Alternatively, using such a system for this use case provides a very low cost, simple, and quick fitting solution, enabling even users in developing nations to have access to such a technology.

Such approach may utilize an incorporated flexible cable within the mesh to control the direction and magnitude of forces more effectively. In a preferred embodiment, the cable may be wound through the holes in the mesh. It may alternatively be attached in any conventional method, such as but not limited to, for example, sewing.

It is contemplated that the cable may consist of various types of materials to accomplish the same, such as but not limited to wires, braided wire, bike cable, plastic rod, rods of various types of materials, and others. Functionally the cable may allow for compliance and bendability, and may hold a form factor to prevent kinking and generally provide a gradual curvature around the body, versus sharp corners. By attaching the cable to the fabric, such as winding it through open mesh, it may provide an anchor point for attachment.

The cable ends may be connected together using any known method of connecting cable ends together. In a preferred embodiment, such cable ends may be connected using elements such but not limited to inserting a small rod, wire, or equivalent into the cable's center and bonding in place. Likewise, it may utilize a sleeve that extends over the ends of the cables, which may then be bonded to the cable. Such sleeve may be strong or rigid or semi-rigid tubing, or may be flexible such as heat shrink. Additionally, any combination of such may be utilized to connect the ends of the cables together. Such methods may allow for simple and quick fabrication for the user, through other methods may be used to accomplish the same.

Now referring to similar man/machine use-cases of such technology, the integration of compliant mesh material, and integrated force distribution cable, may be used in other clinical prosthetics and orthotics applications.

Upper Extremity Harness Interface and Suspension:

In a preferred embodiment a new type of control and suspension harness may be fabricated in such a way as to spread the loads over a broad surface area, it may provide increased resolution of control capabilities, and may generally be more comfortable for the user. In a preferred embodiment, a general vest-type shape may be used, offering a surface area that is significantly greater than a conventional FIG. 8 or FIG. 9 harness. The term vest-type shape should not be considered limiting and it is contemplated that various other shapes may be utilized, although it is understood that any such shape may be considered functionally one and the same in that the shape may generally be used to offer a greater amount of surface area about the user to spread loads.

It is contemplated that various types of materials may be utilized to functionally offer the benefits of such a system, but in a preferred embodiment, a mesh fabric may be used so that it is lightweight, thin, cool, breathable, and compliant over three dimensional shapes such as the human body, and offer a mounting capability for electrodes and sensors.

Now referring to FIG. 8, in a preferred embodiment, general vest harness 800 may be fabricated to fit the user. In general, a vest pattern may utilize simple sewing seams over the tops of shoulders 901, as illustrated in FIG. 9A, and not require any further sewing fabrication. Utilizing open mesh fabric may allow a flat piece of fabric, with seams sewn over the tops of the shoulders, to contour around a three dimensional body, as the open mesh shapes may elongate in various directions.

Such a vest 800 may be sized and fit to the user, and a cable 802, or functionally the equivalent, may be attached to the fabric 801. In a preferred embodiment, the cable 802 may be wound through the holes in the mesh. It may alternatively be attached in any conventional method, such as but not limited to, for example, sewing.

It is contemplated that the cable 802 may consist of various types of materials to accomplish the same, such as but not limited to wires, braided wire, bike cable, plastic rod, rods of various types of materials, and others. Functionally the cable 802 may allow for compliance and bendability, and may hold a form factor to prevent kinking and generally provide a gradual curvature around the body, versus sharp corners. By attaching the cable 802 to the fabric 801, such as winding it through open mesh, it may provide an anchor point for attachment.

Such cable 802 may generally follow a path similar to as shown in FIG. 8, and may generally follow a similar mirrored pattern on the posterior side of the user's torso.

The cable ends may be connected together using any known method of connecting cable ends together. In a preferred embodiment, such cable ends may be connected using elements such but not limited to inserting a small rod, wire, or equivalent into the cable's center and bonding in place. Likewise, it may utilize a sleeve that extends over the ends of the cables, which may then be bonded to the cable. Such sleeve may be strong or rigid or semi-rigid tubing, or may be flexible such as heat shrink. Additionally, any combination of such may be utilized to connect the ends of the cables together. Such methods may allow for simple and quick fabrication for the user, through other methods may be used to accomplish the same.

In a preferred embodiment, such vest harness 800 may extend from the tops of the shoulders, laterally to the sleeve holes, distally to mid range of the torso. Such a layout may offer a great amount of surface area in which for the loads to be dispersed.

On the anterior side of such an apparatus and method, connectors 803 may be used to close the front of such a vest pattern, using straps or webbing, or functionally the equivalent (not shown). In a preferred embodiment, connectors 803 may be used that are simple to operate for one-handed users, such as but not limited to magnetic-based connectors. Such connectors 803 may be modularly connected to the cable 802, such that the connector's connection to the cable 802 provides a broad distribution of forces through the fabric 801, versus isolated loading of the fabric in a tight band. Through such a method, as a little as two connection points on each side of such vest may be sufficient to close the vest and secure the system to the user, although more connectors may be utilized. Such a system may be snug fitting to the user, such that there is negligible motion between it and the user. By utilizing such a large surface area though, such a system does not need to be nearly as tight on the user as a conventional FIG. 8 or FIG. 9 harness (FIG. 13A) may require, as the broader surface area allows for the same amount of force or more to be spread over a broad area and hence provides less force per square inch.

In a preferred embodiment, the distal connectors may be spaced slightly proximal to the distal end of the vest, such that as they are tightened, it may allow for the distal most end of the vest to remain progressively loose, and prevent any roping in or point pressure at the distal end of the fabric. Likewise, the proximal connectors may be modularly positioned such that they may provide a robust and secure lock about the user when forces of the prosthetic control or suspension connections are being used. It is understood that connectors may or may not be parallel, and may be offset from one another to manage the direction of forces.

In a preferred embodiment, additional connectors 804 may be used to attach the vest 800 to the user's prosthetic or orthotic device. Such connectors 804 may be mirrored on the posterior or proximal side of the vest and device such that multiple mounting points may be utilized.

Additional connectors 805 may be used for controls capabilities, such as when using body-powered control of the device. In such an example, connector 805 may be utilized to control an elbow lock function of a prosthetic elbow for instance. It may be connected to the cable 802 on the vest 800, and run to an elbow unit for instance.

Likewise, connectors 1001 may be used for controls capabilities, such as when using body-powered control of a terminal device. It may be connected to the cable on the posterior side of the vest, and preferably the cable on the contrilateral side of the posterior side of the vest, and run to the terminal device for instance.

As has been found clinically, the above described invention provides significantly greater comfort for its users, helps pull the shoulders back, versus forward as in conventional FIG. 8 and FIG. 9 harnesses, making it more comfortable to wear, has negligible point pressures or point specific loading, eliminates loading in the sound side axilla, and provides significantly greater resolution of control when operating body-powered controlled devices such as elbows and terminal devices.

Shoulder Interface and Suspension:

In a preferred embodiment, and much similar to the upper extremity harness interface and suspension method, apparatus, and system described above, the suspension for a user with a shoulder disarticulation or forequarter level amputation, or very short transhumeral amputation, may be utilized. In such an example, the addition of a microframe stabilizing unit 1101 may be utilized to offer a mounting point for a prosthetic shoulder and arm at the shoulder level.

Such stabilizing unit 1101 may be configured in any number of shapes. In general, a mounting point or attachment area 1102 for a prosthetic area or shoulder joint may be utilized at or near the anatomical shoulder area. Additionally, it may consist of a vertical strut or extension 1103 running from or near such shoulder mounting area to its distal end, and may generally run along the lateral side of the body. Distal flanges or equivalent 1104 may be utilized at the distal end to provide rotational stability for the user. Such flanges 1104 may extend around the torso to the front and to the back. The term flanges should not be considered limiting.

In general, the flanges 1104 may extend toward the midline of the body anteriorly and posteriorly. In addition there may be additional flanges 1105 that extend from near the shoulder joint attachment area 1102. Such proximal flanges 1105 may generally extend below the clavicle on the anterior side toward the midline of the body, and the posterior flange may generally extend proximal to the scapula toward the midline. Conventional shoulder level socket designs dig into the delto-pectoral groove on the anterior side and the supraspinatus area on the posterior side, in order to provide suspension control and lock. Instead of aggressively digging into these anatomical grooves, the proximal flanges 1105 may merely wrap around the surface contouring of the body shape and at most may provide slight tissue compression, versus aggressive digging into the muscle grooves to achieve suspension.

In this disclosure, the suspension does not come about through specific digging into the underlying anatomy, but rather is obtained through spreading the loads broadly over the surface area through soft compliant fabric. Hence, surface contouring may be all that is required to achieve the anatomical contouring of such a stabilizing unit. The proximal and distal flanges may be connected together on the anterior and posterior sides of the body, toward their midline ends. The proximal flanges are not required to create a successful interface design, but may add convenient connecting points for the connectors.

Such stabilizing unit may be fabricated from any conventionally used material such as but not limited to resins, laminations, carbon fiber, fiberglass, plastics, and the like. It should be stable enough to hold its general form and orientation, but it is not required to be rigid per-se. The stabilizing unit may merely become a mounting point to hold the prosthetic arm orientation with respect to the user.

The actual interface, or as conventionally referred to as the "socket" may be compliant fabric 1106. Such fabric 1106 may be made of various types of fabric, but in a preferred embodiment, such fabric may be a mesh material, to offer similar benefits as described above in reference to the vest harness application. Such mesh may be attached to the stabilizing unit by VELCRO in various places on the stabilizing unit's anterior side, such as the flanges. The mesh may be attached to the posterior side of the stabilizing unit by connectors 1201. Such connectors 1201 may be any conventional form of connector, but in a preferred embodiment may be on that is simple to donn and doff for one handed use, such as magnetic buckles.

The location of such connectors may generally run from the proximal end of the stabilizing unit side to diagonal across the torso and connect to the sound side cable within the mesh. By doing such, the direction and magnitude of the resultant forces imposed by the prosthetic may be directed across the body of the torso, and away from sensitive areas such as the sound side axilla. This further spreads the loads over the broadest area of the torso. The distal connectors may generally run laterally across the body from the prosthetic side stabilizing unit to the cable within the mesh on the sound side, and may use a slight proximal tilt to the direction of such connector. The connectors may be connected using webbing or the like, functionally. Any such connectors may be adjustable by the user.

On the anterior side, the connectors may be used for donning and doffing of the prosthetic, and physically connecting the vest-shaped garment together, providing suspension and control. The posterior connectors may be used to secure the vest garment to the stabilizing unit and may not be required for donning and doffing. This simplifies the donning and doffing process by only requiring a minimum of one or two connectors on the front of the vest to secure the device in place upon donning. Any such connectors may be adjustable by the user.

It is understood that the pattern to fabricate the shoulder disarticulation vest garment and the pattern to fabricate the FIG. 8 vest garment may be largely similar. A notable difference is that, as illustrated in FIG. 9B, it offers the prosthetic side sewing pattern over the top of the amputated shoulder to contour to body shape, as there may not be an arm to utilize an arm hole.

Prior shoulder disarticulation socket designs, as described by Martin et al. in U.S. Pat. No. 8,840,681 utilized a two-piece fabric pattern, which was significantly harder to donn and doff for one handed users. That prior art design also utilized a significantly larger frame system, which was difficult to use for female users. The stabilizing unit frame section in this disclosure is significantly smaller, lighter, easier to fabricate and fit, and cooler for the user to wear since it covers so much less surface area. The fabric pattern in this disclosure is significantly easier to donn and doff, easier to fabricate and fit, and is significantly more durable.

Similar to the FIG. 8 vest harness design as illustrated in FIG. 9B, a cable may be routed through at least one side of the vest mesh, to create robust and secure mounting points. Such cable may be routed through both sides of the fabric vest.

Limb Orthotic Section:

Now referring to FIG. 14, a cable loop 1401 may be generally attached to connector 1402 to a support structure 1403, which may be attached to an orthotic keel or the like 1404, creating an ankle foot orthotic, knee-ankle-foot orthotic, or other such orthotics.

In such an example, the cable loop 1401 may be similar to that described above in other applications. It may have connectors 1402 that allow it to be modular attached and detached, allowing for the interface itself to be removed from the orthotic device for washing. Such connectors may be any that are commonly used for such connection applications, but in a preferred embodiment may be magnetic-based connectors to allow simplicity in donning and doffing such a device.

Support structure 1403 may be any such flexible strut or equivalent commonly used in the orthotics field, and may then connect to a keel structure as commonly used in the field of orthotics.

Fabric section 1501 may generally be attached to the cable such that it may be pulled snug within the cable span, creating a hammock or drum effect. The integration of the cable with the fabric may together create a structure element that may be spanned over a portion of the body segment. As such a cable may be connected to the fabric, such as winding the cable through the loops of open mesh fabric, the two may become one structural element. The length of the cable within the fabric may be adjusted such that there may be an overtightened amount of cable within a given loop of fabric, creating a "pringle" shaped panel of fabric, and structure. A similar effect may be observed in other described applications including for use in upper extremity vest harness applications. This induces the perimeter edges of such a system to pull away from the body, mitigating roping in or edge pressure in such areas.

Fabric extension 1502 may generally extend from an edge of the pringle shaped panel and may be used to wrap around a limb and connect to the contrallateral side, as illustrated in FIG. 16. Such a system may as well utilize connectors to attach the extension panel to the pringle shaped panel.

Alternatively, opposing pringle shaped panels, using cable wound through the fabric for instance, may be connected together as front and back panels, creating a similar final outcome, as is illustrated in FIG. 15B.

Conversely, conventional orthotic cuffs use foam padding and VELCRO straps to connect to the limb segments. Such a configuration becomes hot, is not breathable, and induces higher forces per square inch of surface because there is a smaller amount of surface area covered.

In this disclosure however, the open mesh fabric, with a cable, which holds the fabric in a particular orientation about the limb provides a highly breathable interface, very lightweight, conforms to the underlying body, is cool, and is much less expensive and greatly simplified to custom fit to the user.

FIG. 17 generally illustrates a modular support structure, which may be custom fabricated to match the user's dynamic biomechanical ambulation needs. Such a system may utilize struts, tubes, tent poles, rods, or other functionally similar materials, any of which may be made from resins, plastics, laminates, metals, fibers, carbon fibers, fiberglass, or other such materials. Additionally, 3D printable inserts may be inserted in between, attached to, or incorporated within such a structure to modularly alter the dynamic characteristics of such a system.

FIG. 18 generally illustrates a similar embodiment, but for a knee orthosis, whereas the cables, and associated fabric, may be modularly connected to support structures. Similar approaches using cable integrated within fabric may be used to span around limb segments for any orthotic level including both upper and lower extremity applications.

Exoskeletal Robotics Interface:

In much the same way as described and illustrated for clinical orthotic applications, similar methods may be utilized for exoskeletal robotic applications. Exoskeletal robotics are merely advanced robotic orthotic devices.

Exoskeleton devices often have additional support structures integrated within which fabric sections may be spanned between. In a preferred embodiment, the use of a cable integrated within such fabric, within such a structure may be advantageous as it can effectively balance and control a distribution of forces more effectively than a rigid structure alone.

The integration of such a method within exoskeletal robotics may functionally be highly similar to the clinical orthotics methods, as well as the upper extremity torso section methods.

By way of example, a vest similar to that of the vest harness section described above may be used to control and mount the torso body segment within an exoskeleton device. Similarly, the backpack carryall method described above may as well be used to mount the torso body segment within an exoskeleton device. Likewise, a combination of the two together may be use to mount the torso body segment within an exoskeleton device. By doing so, the torso interface may be connected to any remaining structure such that it may provide a biomechanical lock between the user's torso and the exoskeleton device. Such an interface has been shown to have minimal to negligible movement between the user and the device in clinical applications.

The use of fabric mesh with the integrated cable provides a broad distribution of forces about the body, is cool, provides effective mounting points for control and sensor integration, and provides a comfortable interface with low force per square inch, yet is highly biomechanically locked about the body.

Likewise, instead of connecting the limb interface segments of the clinical ankle foot orthotic to support structure 1403 of the ankle foot orthotic, it may instead be connected to an integrated support structure of the exoskeleton robotic device. The same application can be found in upper or lower extremity use of orthotics or exoskeletal robotics.

Similar methods may be utilized in fitting prosthetic extremity interfaces as well, including transfemoral interfaces, transtibial interfaces, transhumeral interfaces, or transradial interfaces. In such examples, the socket interface section may comprise at least one fabric section about the limb, which may utilize a cable integrated within such fabric section to effectively control the dynamic forces through the fabric about the body. Such section may span between or among biomechanical stabilizing units to effectively control tissue, and increase device comfort, and device control.

These sections may look and function highly similar to the use-case of the ankle foot orthotic pringle section, but may be attached to stabilizing unit sections, in order to create a broad panel in which to control tissue and limb segments.

FIG. 19 generally represents a pringle shaped compliant panel fabricated from fabric with integrated cable. Such a system may utilize connectors 1901, which may allow for the panel to be stretched around a limb segment and connected to a stabilizing unit, creating a stabilized limb and tissue segment for prosthetics applications. Such a panel may remain breathable, cool, lightweight, and compliant as it may be fabricated from lightweight mesh and cable materials.

Such methods and devices may allow a more comfortable and functional connection between the user and the device by better managing tissue and spreading loads more effectively, providing a more gradual force transition throughout the interface, provide a greater biomechanical lock about the body, and decrease movement between the device and its user.

Changes may be made in the combinations, operations, and arrangements of the various parts and elements described herein without departing from the spirit and scope of the invention. Furthermore, names, titles, headings and general division of the aforementioned are provided for convenience and should, therefore, not be considered limiting.

I claim:

1. A compliant force distribution system to suspend loads around a user's ankle and foot comprising:
    a keel adapted to be positioned under said user's foot with a surface area that is approximately the same size as the distal surface portion of said user's foot;
    a flexible support structure having a proximal end and a distal end, said distal end being connected to said keel and said proximal end adapted to extend to the proximal end of said user's gastrocnemius;
    a compliant fabric member adapted for positioning around the anterior of said user's tibia above said user's ankle having an integrated cable adapted to be located on said user's medial and lateral sides of said user's tibia which is then routed through said fabric member, wherein said cable spreads connection loads over a broad area of said user's tibia and said fabric member; and
    at least one attachment point for connecting said loads to said fabric member.

2. The system of claim 1 wherein said compliant fabric member is made from a compliant mesh fabric.

3. The system of claim 1 wherein said attachment point is connected to said cable.

* * * * *